US008551486B2

(12) United States Patent
Lallatin

(10) Patent No.: US 8,551,486 B2
(45) Date of Patent: *Oct. 8, 2013

(54) MONOCLONAL ANTIBODIES TO HUMAN THYMIDINE KINASE TO TREAT CANCER

(75) Inventor: Nathaniel C. Lallatin, Park City, UT (US)

(73) Assignee: Savoy Pharmaceuticals, Inc., Provo, UT (US)

( * ) Notice: Subject to any disclaimer, the term of this patent is extended or adjusted under 35 U.S.C. 154(b) by 21 days.

This patent is subject to a terminal disclaimer.

(21) Appl. No.: 12/328,379

(22) Filed: Dec. 4, 2008

(65) Prior Publication Data

US 2010/0143244 A1    Jun. 10, 2010

Related U.S. Application Data

(63) Continuation-in-part of application No. 11/134,854, filed on May 20, 2005, now Pat. No. 7,837,998.

(60) Provisional application No. 60/573,429, filed on May 21, 2004.

(51) Int. Cl.
*A61K 39/00*      (2006.01)

(52) U.S. Cl.
USPC ........................................................ 424/155.1

(58) Field of Classification Search
None
See application file for complete search history.

(56) References Cited

U.S. PATENT DOCUMENTS

| | | | |
|---|---|---|---|
| 4,317,877 | A | 3/1982 | Balis et al. |
| 4,474,893 | A | 10/1984 | Reading |
| 4,722,899 | A | 2/1988 | Hamaoka et al. |
| 4,816,567 | A | 3/1989 | Cabilly et al. |
| 5,476,996 | A | 12/1995 | Wilson et al. |
| 5,514,548 | A | 5/1996 | Krebber et al. |
| 5,698,409 | A | 12/1997 | O'neill |
| 5,869,045 | A | 2/1999 | Hellstrom et al. |
| 6,083,707 | A | 7/2000 | Eriksson et al. |
| 6,331,415 | B1 | 12/2001 | Cabilly et al. |
| 6,372,217 | B1 | 4/2002 | Uckun |
| 7,311,906 | B2 | 12/2007 | Lallatin et al. |
| 2003/0148410 | A1 | 8/2003 | Berger et al. |
| 2006/0039914 | A1 | 2/2006 | Lallatin et al. |
| 2007/0003990 | A1* | 1/2007 | Schlegel et al. ............. 435/7.23 |

FOREIGN PATENT DOCUMENTS

| | | |
|---|---|---|
| EP | 0042482 | 12/1981 |
| EP | 0255431 | 10/1991 |
| EP | 0454478 | 10/1991 |
| WO | 9306213 | 4/1993 |
| WO | 9529192 | 11/1995 |
| WO | 9708320 | 3/1997 |

OTHER PUBLICATIONS

Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
AbNova website search (TK1 antibody; pp. 1-3; Sep. 6, 2011).*
Horio Masaru et al. "ATP-dependent transport of vinblastine in vesicles from human multidrug-resistant cells," Proc. Natl. Acad. Sci. USA 85:3580-3584.
U.S. Appl. No. 60/567,344, filed Apr. 30, 2004, Lallatin.
Balzarini et al. (1982) "Role of Thymidine Kinase in the Inhibitory Activity of 5-Substitued-2'Deoxyuridines on the Growth of Human and Murine Tumor Cell Lines," Biochem. Pharmacol. 31(6):1089-1095.
Baron et al. (1990) "A Rapid Two-Step Purification of Rat Liver Fetal Thymidine Kinase," Preparative Biochem. 20 (3-4):241-256.
Boivin et al. (2002) "Intranasal Herpes Simplex Virus Type 2 Inoculation Causes a Profound Thymidine Kinase Dependent Cerebral Inflammatory Response in the Mouse Hindbrain," Eur. J. Neurosci. 16(1):29-43.
Bradshaw, H.D. Jr. (1983) "Molecular Cloning and Cell-Specific Regulation of a Functional Hyman Thymidine Kinase Gene," Proc. Natl. Acad. Sci. USA 80:5588-5591.
Bronzert et al. (1981) "Purification and Properties of the Estrogen-Responsive Cytoplasmic Thymidine Kinase from Human Breast Cancer," Cancer Res. 41:604-610.
Daugherty, et al. (1991) "Polymerase Chain Reaction Facilitates the Cloning, CDR-Grafting, and Rapid Expression of a Murine Monoclonal Antibody Directed Against the CD18 Component of Leukocyte Integrins," Nuc. Acids Res. 19 (9):2471-2476.
Ellims et al. (1982) "Human Thymidine Kinase: Purification and Some Properties of the TK1 Isoenzyme from Placenta," Mol. Cell. Biochem. 45:113-116.
Flemington (1987) "Sequence, Structure and Promoter Characterization of the Hyman Thymidine Gene," Gene 52:267-277.
Gan et al. (1983) "Human Thymidine Kinase," J. Biol. Chem. 258:7000-7004.

(Continued)

*Primary Examiner* — Brad Duffy
*Assistant Examiner* — Nelson B Moseley, II
(74) *Attorney, Agent, or Firm* — Pate Baird, PLLC

(57) ABSTRACT

A method of treatment of cancer, viral infections, and the like administers anti-TK1 antibody, constituted as the complete antibody or a fragment thereof. The antibody binds to the surface of cells expressing TK1 thereon. The antibody, with or without another agent bound thereto, may effect complement mediated lysis, antibody-dependent cell-mediated cell cytotoxicity, apoptosis, an immune response by the mammal, a reduction in cellular replication, a combination thereof, or the like for such cells. The antibody may be coupled to an immune response stimulator, a cytotoxin, an enzyme, a combination, or the like to effect the treatment desired.

7 Claims, 18 Drawing Sheets

(56) References Cited

OTHER PUBLICATIONS

Goding et al. (1980) "Antibody Production by Hybridomas," J. Immunol. Methods 39:285-308.
Gronowitz et al. (1984) "Application of an In Vitro Assay for Serum Thymidine Kinase: Results on Viral Disease and Malignancies in Humans," Int. J. Cancer 33:5-12.
Habteyesus et al, (1991) "Deoxynucleside Phosphorylating Enzymes in Monkey and Human Tissues Show Great Similarities, While Mouse Deoxycytidine Kinase has a Different Substrate Specificity," Biochem. Pharmacol. 42)9): P1829-P1836.
Hannigan et al. (1993) "Thymidine Kinase: The Enzymes and Their Clinical Usefulness," Cancer Biother. 8(3):187-197.
Chatterjee et al., Cancer Immunol. Imunother., 38:75-82, 1994.
He et al. Cell Prolif. 35(2):69-81 (2002).
ATCC website search of HB11432 (pp. 1-2).
ATCC website search of HB11433 (pp. 1-2).
ATCC website search of HB11434 (pp. 1-2).
He, Q. et al. "The clinical significance of thymidine kinase 1 measurement in serum of breast cancer patients using anti-TK1 antibody," The International Journal of Biological Markers, Apr.-Jun. 2000, vol. 15, No. 2, pp. 139-146.
Nesterova, M. et al. "Autoantibody biomarker opens a new gateway for cancer diagnosis," Biochimica et Biophysica Acta 1762 (2006) 398-403.
Wu, Chuanjing et al. "Production and characterization of a novel chicken IgY antibody raised against C-terminal peptide from human thymidine kinase 1," Journal of Immunological Methods, Jun. 1, 2003, vol. 277, No. 1-2, pp. 157-169.
Yagihashi, Atsuhito et al. "Detection of autoantibodies to survivin and livin in sera from patients with breast cancer," Clinica Chimica Acta 362 (2005) 125-130.
Zhang, Jian-Ying et al. "Enhancement of Antibody Detection in Cancer Using Panel of Recombinant Tumor-associated Antigens," Cancer Epidemiology, Biomarkers & Prevention, 2003, vol. 12, 136-143.
Voskoglou-Nomikos (Clin. Can. Res. 9:4227-4239) (2003)).
Hengstschlager et al. (1994) "Different Regulation of Thymidine Kinase During the Cell Cycle of Normal Versus DNA Turmor Virus-Transformed Cells," J. Biol. Chem. 269:13836-13842.
Hengstschlager et al. (1994) "A Common Regulation of Genes Encoding Enzymes of the Deoxynucleotide Metabolism is Lost After Neoplastic Transformation," Cell Growth Differ. 5(12):1389-1394.
Hengstschlager et al. (1993) "Cytofluorometric Assay for the Determination of Thymidine Uptake and Phosphorylation in Living Cells," Cytometry 14:39-445.
Jansson et al. (1992) "Mammalian Thymidine Kinase 2, Direct Photoaffinity Labeling with [32P]dTTP of the Enzyme from Spleen, Liver, Heart and Brain," Eur. J. Biochem. 206(2):485-490.
Kohler et al. (1976) "Derivation of Specific Antibody-Producing Tissue Culture and Tumor Lines by Cell Fusion," Eur. J. Immunol. 6:511-519.
Lau et al. (1994) "Direct Isolation of the Functional Human Thymidine Kinase Gene W/A Cosmid Shuttle Vector," Proc. Natl. Acad. Sci. USA 81:414-418.
May et al. (1991) "intracellular Routing Rather than Cross-Linking or Rate of Internalization Determines the Potency of Immunotoxins Directed Against Different Epitopes of slgD on Murine B Cells," Cell Immunol. 135:490-500.
McKenna et al. (1988) "Thymidine Kinase Activities in Mononuclear Leucocytes and Serum from Breast Cancer Patients," Br. J. Cancer 57:619-622.
Munch-Peterson et al. (1990) "Thymidine Kinase in Human Leukemia—Expression of Three Isoenzyme Variants in Six Patients with Chronic Myelocytic Leukemia," Leuk Res. 14:39-45.
Munch-Peterson et al. (1991) "Diverging Substrate Specificity of Pure Human Thymidine Kinases 1 and 2 Against antiviral Dideoxynucleosides," J. Biol. Chem. 266:9032-9038.
Munch-Peterson et al. (1993) "Reversible ATP-Dependent Transition Between Two Forms of Human Cytosolic Thymidine Kinase With Different Enzymatic Properties," J. Biol. Chem. 268(21):15621-15625.
Oldham et al. (1993) "Whats the Score," Cancer Biother. 8(3):187-188.
O'Neill et al. (1992) "Can Thymidine Kinase Levels in Breast Tumors Predict Disease Recurrence," J. Nat. Cancer Inst. 84(23):1825-1828.
O'Neill et al. (1987) "Elevated Serum and Mononuclear Leukocyte Thymidine Kinase Activities in Patients with Cancer," Irish Med. J. 80(9):264-265.
Seaver et al. (1994) "Monoclonal Antibodies in Industry: More Difficult Than Originally Thought," Genetic Eng. News pp. 10, 21.
Sherley et al. (1988) "Human Cytosolic Thymidine Kinase," J. Biol. Chem. 263:375-391.
Tamiya et al. (1989) "Co-Purification of Thymidylate Kinase and Cytosolic Thymidine Kinase from Human Term Placenta by Affinity Chromatography," Biochem. Biophys. Acta 005:28-35.
Topoclan et al. (2005) "Changes of Thymidine Kinase (TK) During Adjuvant and Palliative Chemotherapy," Anticancer Res. 25:1831-1834.
Willingham et al. (1987) "*Pseudomonas* Exotoxin Coupled to a Monoclonal Antibody Against Ovarian Cancer Inhibits the Growth of Human Ovarian Cancer Cells in a Mouse Model," Proc. Natl. Acad. Sci. USA 84:2474-2478.
Search results from ATCC website for "CB100" and "PTA—6704" (pp. 1-2).
Fundamental Immunology 242 (William E. Paul, M.D. ed., 3d ed. 1993).
Jain, Scientific American Jul. 1994 pp. 58-65.
Dennis (Nature 442: 739-741(2006)).
Cespdes et al. (Clin. Transl. Oncol. 8(5):318-329 (2006)).
Salfeld (Nature Biotech. 25(12); 1369-1372 (2007)).
Carter et al. (1992) "Humanization of an anti-p185 her2 antibody for human cancer therapy," Proc. Natl. Acad. Sci. USA, 89:4285-4289.
Co et al. (1994) "A Humanized Antibody Specific for the Platelet Integrin gpIIb/IIIa," Journal of Immunology, 152: 2968-2976.
Robinson et al. (2004) "Improving Monoclonal Antibodies for Cancer Therapy," Drug Development Research, 61:172-187.
Sato, Koh et al. "Reshaping a Human Antibody to Inhibit the Interleukin 6-dependent Tumor Cell Growth," Cancer Research 53, 851-856 (1993).

* cited by examiner

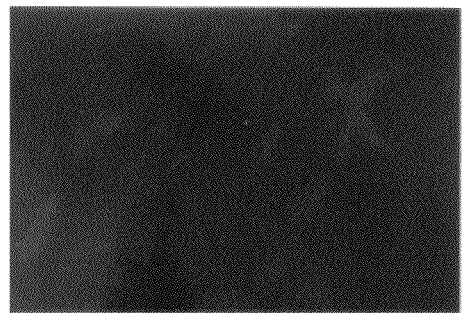
Fig. 13    Fig. 14
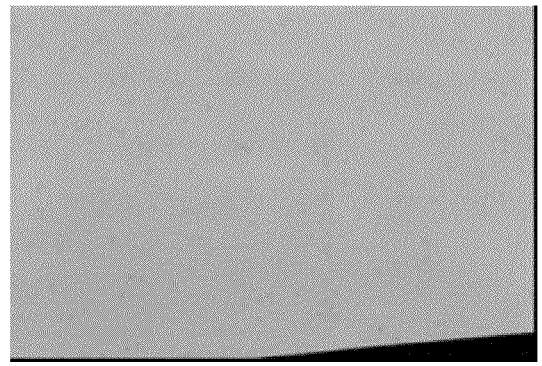
Fig. 15
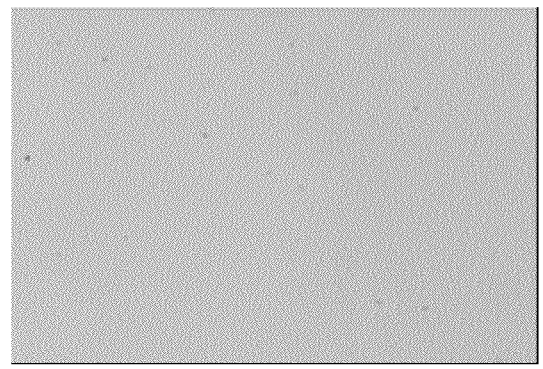
Fig. 16

Murine Tumor Xenograft – Colon Cancer

Results for the HCT116-e249 Study

| Group | n | Treatment Regimen ||||  Median ||| Statistical Significance | MTV (n) Day 27 | No. of PR | No. of CR | No. of TFS | Mean BW Nadir | No. of TR | No. of NATR |
|---|---|---|---|---|---|---|---|---|---|---|---|---|---|---|---|---|
| | | Agent | µg/ mouse | Route | Schedule | TTE | T-C | TGD | | | | | | | | |
| 1 | 5 | Vehicle | - | i.t. | biwk x4 | 14.1 | --- | --- | --- | --- | 0 | 0 | 0 | --- | 0 | 0 |
| 2 | 5 | TO1 | 50 | i.t. | biwk x4 | 18.4 | 4.3 | 30% | ns | --- | 0 | 0 | 0 | --- | 0 | 0 |
| 3 | 5 | TO1 | 50 | i.p. | biwk x4 | 16.3 | 2.2 | 16% | ns | --- | 0 | 0 | 0 | --- | 0 | 0 |

*Dose = µg/animal

Study Endpoint = 1000 mm$^3$, Days in Progress = 27
N = number of animals in a group not dead from accidental or unknown causes, or euthanized for sampling
MTV (n) = median tumor volume (mm$^3$) for the number of animals on the day of TGD analysis (excludes animals with tumor volume at endpoint)
TTE = time to endpoint, T-C = difference between median TTE (days) of treated versus control group, %TGD = [(T-C)/C] x 100
Statistical Significance = Logrank test: ns = not significant, * = $P<0.05$,  = $P<0.01$, * = $P<0.001$, compared to Group 1
PR = partial regression, CR = complete regression, TFS = tumor free survivor
Mean BW Nadir = lowest group mean body weight, as % change from Day 1; ---indicates no decrease in mean body weight was observed
TR = treatment-related death, NTR=non-treatment-related death

Fig. 36

Treatment Response Summary for the MDA-MB231-e253 Study

| Group | n | Treatment Regimen 1 | | | | Median | | | Significant Significance | | | | | | MTV(n) | Regressions | | | Mean BW | Deaths | |
|---|---|---|---|---|---|---|---|---|---|---|---|---|---|---|---|---|---|---|---|---|---|
| | | Agent | Mg/kg | Route | Schedule | TTE | T-C | %TGD | vs G1 | vs G2 | vs G4 | vs G6 | vs G7 | vs G8 | Day 59 | PR | CR | TFS | Nadir | TR | NTR |
| 1 | 10 | No Treatment | - | - | - | 25.0 | --- | --- | --- | --- | --- | --- | --- | --- | --- | 0 | 0 | 0 | --- | 0 | 0 |
| 2 | 9 | Paclitaxel | 3 | i.v. | qod x5 | 26.5 | 1.5 | 6 | * | --- | --- | --- | --- | --- | --- | 0 | 0 | 0 | --- | 0 | 1 |
| 3 | 10 | Paclitaxel | 30 | i.v. | qod x5 | 59.0 | 34.0 | 136 | *** | --- | --- | --- | --- | --- | 63 (10) | 0 | 10 | 2 | -4.6% Day 14 | 0 | 0 |
| 4 | 10 | B-glucan | 16 | p.o | qd x28 | 27.4 | 2.4 | 10 | * | --- | --- | --- | --- | --- | --- | 0 | 0 | 0 | --- | 0 | 0 |
| 6 | 10 | TO1 | 15 | i.v. | biwk x4 | 27.5 | 2.5 | 10 | * | | | | | | | 0 | 0 | 0 | | 0 | 0 |
| 11 | 10 | TO1<br>Paclitaxel | 75<br><br>3 | i.v.<br><br>i.v. | bid on days | 27.4 | 2.4 | 10 | * | ns | --- | --- | --- | * | --- | 0 | 0 | 0 | -1.4% Day 2 | 0 | 0 |
| 12 | 10 | TO1<br>B-glucan | 15<br>16 | i.v.<br>p.o. | biwk x4<br>qd x28 | 30.5 | 5.5 | 22 | *** | | ns | ns | | | | 0 | 0 | 0 | | 0 | 0 |

*µg/animal
Study Endpoint = 1500 mm³, Days in Progress = 59
n = number of animals in a group not dead from accidental or unknown causes, or euthanized for sampling
TTE = time to endpoint, T-C = difference between median TTE (days) of treated versus control group, %TGD = [(T-C)/C] x 100
Statistical Significance = Logrank test: ns = not significant, * = $P < 0.05$, ** = $P < 0.001$, compared to Group 1
MTV(n) = median tumor volume (mm³) for the number of animals on the day of TGD analysis (excludes animals attaining the tumor volume endpoint)
PR = partial regression; CR = total number complete regressions; TFS = tumor free survivors, i.e., CRs at end of study
Mean BW Nadir = lowest group mean body weight, as % change from Day 1;--- indicates no decrease in mean body weight was observed
TR = treatment-related death; NTR = non-treatment related death

Fig. 37

Table 1 - FDA 33 Normal Tissue Panel with Oncoprev™

| Organ | # patients | Age | Sex | Pathology Diagnosis | % stained | Staining strength |
|---|---|---|---|---|---|---|
| Adrenal gland | 3 | 14, 1 mo, 5 mo | F,M,M | Adrenal gland tissue | 0 | - |
| Bladder | 1 | 21 | F | Fibrous tissue | 0 | - |
| Bone Marrow | 3 | 50,77,22 | M,F,M | Bone Marrow Tissue | 0 | - |
| Breast | 3 | 21,21,35 | F,F,F | Fibrofatty, fibrous, breast tissue | 0 | - |
| Cerebellum | 3 | 24,58,8 | F,F,F | Cerebellum tissue | 0 | - |
| Cerebrum | 3 | 2,50,42 | F,F,F | Cerebrum tissue | 0 | - |
| Colon | 3 | 42,35,30 | F,M,M | Colon tissue | 0 | - |
| Espophagus | 3 | 42,18,21 | F,F,F | Esophagus tissue | 0 | - |
| Fallopian tube | 3 | 21,26,46 | F,F,F | Fallopian tube | 0 | - |
| Heart | 3 | 56,42,35 | M,F,F | Cardiac muscle tissue | 0 | - |
| Hypophysis | 3 | 15,17,56, | F,F,F | Hypophysis tissue | 0 | - |
| Kidney | 3 | 16,48,38 | M,M,F | Kidney tissue | 0 | - |
| Liver | 3 | 14,2,35 | F,F,F | Liver tissue | 0 | - |
| Lung | 3 | 24,42,49 | M,M,M | Liver tissue | 0 | - |
| Mesothelial tissue | 3 | 22,21,18 | M,F,F | Lung tissue | 0 | - |
| Nerve | 3 | 48,27,25 | F,M,F | Lung and mesothelial tissue | 0 | - |
| Ovary | 3 | 62.15,21 | F,F,F | ovary tissue | 0 | - |
| Pancreas | 3 | 42,35,30 | M | pancreas tissue | 0 | - |
| Placenta | 3 | 42,18,21 | M | Placenta tissue | 0 | - |
| Prostate | 3 | 56,42,35 | M,M,M | Prostate tissue | 0 | - |
| Salivary Gland | 3 | 50, 77,22 | M,M,M | Salivary gland tissue | 0 | - |
| Skin | 3 | 40,21,19 | F,F,M | Skin tissue | 0,0,1 | - - + |
| Small intestine | 3 | 15,48,38 | M,F,M | Small intestine tissue | 0 | - |
| Spleen | 3 | 30,65,74 | F | Spleen tissue | 0 | |
| Stomach | 3 | 14,2,35 | 2,35,24 | Stomach tissue | 0 | - |
| Striated muscle | 3 | 27,21,2` | F,M,M | Skeletal muscle tissue | 0 | - |
| Testis | 3 | 30,65,74 | M,M,M | Testis tissue | 0 | - |
| Thymus | 3 | 24,42,49 | F,M,M | Thymus gland tissue | 0 | - |
| Thyroid | 6 | 40,21,19,21,40,35, | 3F,3M | Thyroid tissue | 0 | - |
| Tonsil | 3 | 30,30,52 | F,M,M | Tonsil tissue | 0 | - |
| Ureter | 3 | 56,37,72 | M,F,M | Ureter tissue | 0 | - |
| Uterine Cerivix | 3 | 272,121 | F,F,F | Uterine cervix tissue, Fibrous tissue and blood vessel | 0 | - |
| Uterus | 3 | 20,35,28 | F,F,F | Endometrium tissue | 0 | - |

Criteria for Scoring

0 = 0% of the cell population are positive
1 = 1 to 15% of the cell population are positive
2 = 16 to 25% of the cell population are positive
3 = 26 to 50% of the cell population are positive
4 = 51 to 75% of the cell population are positive
5 = 76 to 100% of the cell population are positive

- = Negative staining
+ = Weak staining intensity
++ = Medium staining intensity
+++ = Strong staining intensity

Fig. 38

Table 2: Multiple Organs, Tumor Screen Panel TMA with Oncoprev™

| No. Samples | Gender | Organ | Pathology Diagnosis | Avg. Grade | % stained | Staining strength |
|---|---|---|---|---|---|---|
| 40 | F | cervix | Squamous cell carcinoma | III | N/A | |
| 3 | FFF | Bladder | Squamous cell carcinoma | I/II | 0,0,4 | -,-,++++ |
| 3 | FFF | Breast | carcinoma | I/III | 0,0,5 | -,-,+++ |
| 2 | MMF | cervix | Squamous cell carcinoma | II | 0,2 | -,+++ |
| 3 | MMF | s | Squamous cell carcinoma | III | 0,0,2 | -,-,+ |
| 3 | FFF | Lung | Clear cell carcinoma | III | 0,1,0 | -,+,- |
| 2 | FF | Ovary | Endometrioid carcinoma | III | 1, 2 | +,++ |
| 3 | FFM | Ovary | Adenocarcinoma | III | 1 | ++ |
| 3 | MFF | Pancreas | Adenocarcinoma | III | 0,0,1 | -,-,++ |
| 31 | 13F, 18M | Rectum | Malignant Melanoma | I/III | Average 2 to 3 | Average ++ |
| 3 | FMM | Skin | various | III | 0,4,5 | -,+,++ |
| 7 | F | Skin | Skin Vulva | III | 1 | +/+++ |
| 3 | MMM | Skin | Adenocarcinoma | III | 3 | ++ |
| 3 | MFF | Stomach | Papillary carcinoma | II | 1 | ++ |
| 2 | FMM | Thyroid | Transitional cell carcinoma | I/II | 3,4 | +,++ |

Criteria for Scoring

0 = 0% of the cell population are positive
1 = 1 to 15% of the cell population are positive
2 = 16 to 25% of the cell population are positive
3 = 26 to 50% of the cell population are positive
4 = 51 to 75% of the cell population are positive
5 = 76 to 100% of the cell population are positive

- = Negative staining
+ = Weak staining intensity
++ = Medium staining intensity
+++ = Strong staining intensity
N/A = Tissue depletion

Fig. 43

MONOCLONAL ANTIBODIES TO HUMAN THYMIDINE KINASE TO TREAT CANCER

This application is a continuation-in-part of U.S. patent application Ser. No. 11/134,854, filed on May 20, 2005 now U.S. Pat. No. 7,837,998, which is incorporated herein by reference, which claims the benefit of U.S. Provisional Patent Application Ser. No. 60/573,429, filed on May 21, 2004.

BACKGROUND

1. The Field of the Invention

The invention relates to treatment of cancer and viral infections and more particularly to therapies using a monoclonal antibody to thymidine kinase.

2. The Background Art

Thymidine kinase (ATP:thymidine-5' phosphotransferase; EC 2.7.1.21 in the International Union of Biochemistry classification system) is an enzyme that phosphorylates thymidine to thymidine monophosphate (TMP). The commonly used abbreviation of TK will be used herein to denote thymidine kinase in a general sense, where different TK isozymes are not specified particularly.

Thymidine kinase protein has been isolated from many different sources and purified to varying degrees. A variety of different molecular weight thymidine kinases have been reported from human samples, depending on the particular cell and the method of isolation and analysis. In general, thymidine kinase may exist in at least one monomeric form and a variety of multimeric forms.

In humans, there are at least two major isozymes (similar but distinct forms) of thymidine kinase, referred to herein as TK1 and TK2. These isozymes are produced from different genes, are found in different cellular compartments, and differ in their levels and timing of expression during the cell cycle and according to the cell differentiation state. In humans, the TK1 gene is on chromosome 17 in band q21-22 while the TK2 gene is on chromosome 16. A gene for TK1 has been cloned and sequenced.

There are extensive inconsistent reports in the prior art on the properties of mammalian TK1, with diverging results and observations as to the electrophoretic behavior and kinetic properties. Native molecular weights between 45,000 and 200,000 Daltons (or kilo Daltons, kD) have been reported for the native human TK1 from, for example, leukemic cells at 96 kD versus 150-200 kD, human placenta cells at 45 kD versus 92 kD versus 70 kD, lymphocytes at 110 kD, and human breast cancer cells 177 kD.

TK1 has been observed in serum associated with cancerous mammals. However, no prior art studies or papers known to Applicant propose a plausible transport mechanism moving TK1 from its location of origin inside a cell to serum outside the cell. What is needed is an understanding of the transport processes and biological activity of TK1 in order to use this "evidence" of cancerous cell-division activity to develop a therapy useful to mark and treat cancers, viruses, and the like, which hijack cell division structures and chemistry to propagate themselves and infected cell structures.

SUMMARY OF THE INVENTION

In accordance with the invention, the physical transport processes controlling expression of TK1 were considered in order to characterize its behavior. Likewise, Applicant was first to learn that TK1 is expressed on the surface of cells, that it is expressed on the surface of cells of all known cancer types and of virus infected cells, that is not expressed on the surface of normal or healthy cells, and that anti-TK1 antibodies may be used to identify, target, attach to, and treat a cell expressing TK1 on the surface thereof. Also, in accordance with the invention other agents may be bound to anti-TK1 antibodies or fragments of anti-TK1 antibodies to inhibit replication, modify functioning of cells, and kill cells by complement mediated lysis, antibody-dependent cell-mediated cell cytotoxicity, apoptosis, an immune response by the mammal, or the like.

In some embodiments, the invention is directed to a method for treating cancer in a mammal. It may include administering to the mammal, an amount of a pharmaceutical composition that includes an anti-TK1 antibody or fragment thereof, sufficient to kill cancer cells or inhibit cancer cell replication. The anti-TK1 antibody may be a monoclonal antibody. One suitable anti-TK1 monoclonal antibody is Oncoprev™.

In some embodiments, the anti-TK1 antibody is a humanized or fully human monoclonal antibody. In some alternative embodiments, the anti-TK1 antibody may be conjugated to a cytotoxic agent such as pokeweed anti-cancer protein (PAP), ricin, abrin, gelonin, saporin, alpha-sarcin, or the like.

In some embodiments, prior to administering a pharmaceutical composition, the mammal is treated with sufficient radiation to up-regulate TK1 expression. In some embodiments, the pharmaceutical composition also includes a pharmaceutically acceptable liquid carrier adapted for parenteral administration, such as, for example isotonic saline.

In some embodiments, the invention is directed to a method for diagnosing cancer in a mammal, and may include obtaining a sample from a mammal, incubating the sample with an anti-TK1 antibody or fragment thereof, detecting an amount of antibody-TK1 complex, quantifying the concentration of TK1 in the sample by comparing the detected amount of antibody-TK1 complex with a standard curve generated using known amounts of TK1, and diagnosing the presence of cancer in the mammal based on the concentration of TK1 in the sample.

In one embodiment, a method of treatment may include providing an anti-TK1 antibody and administering it to a mammal. The antibody may be constituted as the complete antibody or a fragment of the antibody. The antibody binds to the surface of cells expressing TK1 on the surfaces thereof. The antibody, with or without another agent bound thereto may effect complement mediated lysis, antibody-dependent cell-mediated cell cytotoxicity, apoptosis, an immune response by the mammal, a reduction in cellular replication, a combination thereof, or the like.

For tumor cells, one embodiment of a method in accord with the invention relies on coupling the antibody to an anti-tumor agent. The agent then effects destruction of a disproportionately greater fraction of the tumor cells than non-tumor cells.

In one embodiment, the antibody is a monoclonal antibody. In any event, treatment may involve administering a therapeutically effective amount of the antibody, which may be coupled to one or more of an immune response stimulator, a cytotoxin, an enzyme, or a combination thereof. The agent selected to effect at least one of the complement mediated lysis, antibody dependent cell mediated cell cytotoxicity, apoptosis, and reduction of cellular replication.

The antibody is more effective if monoclonal, and may be provided in a kit. Also, in certain embodiments, a therapeutic substrate may be bound to the anti-TK1 antibody in order to treat a cell by the therapeutic substrate being delivered to the cell upon binding of the antibody to surface TK1 of the cell.

In one embodiment, a method for treating cancer may rely on the increased expression of TK1 by cancer cells in a mammal. Administering to the mammal a therapeutically effective amount of a pharmaceutical composition comprising at least one of an anti-TK1 antibody and a fragment of the anti-TK1 antibody selected to be effective to do at least one of inhibit cellular replication of cancer cells and kill cancer cells. An anti-TK1 monoclonal antibody found to be effective is available from AbNova, and designated as the H00007083-M02 antibody, and also known by Applicant's trademark Oncoprev™. A humanized, a fully human monoclonal antibody, or both may be used in methods in accordance with the invention.

A suitable pharmaceutical composition may include a second anti-cancer agent in addition to the antibody acting as a first anti-cancer agent. The second anti-cancer agent may be selected, for example, from the Alkylating agents including nitrogen mustards, nitrosoureas, alkyl sulfonates, triazines, ethylenimines, taxanes, epothilones, vinca alkaloids, estramustine, corticosteroids, L-asparaginase, targeted therapy agents, hormone therapy agents, immunotherapy agents, adjuvants, immunomodulating drugs, cancer vaccines, or the like.

Also, the second anti-cancer agent may be selected from the group consisting of nucleoside analogs, non-nucleoside analogs, protease inhibitors, and entry inhibitors.

The anti-TK1 antibody may be conjugated to a cytotoxic agent. That cytotoxic agent may be selected from, for example, pokeweed anti-cancer protein (PAP), ricin, abrin, gelonin, saporin, TNF-alpha-sarcin, or the like.

In one embodiment, treatment of a mammal with an amount of radiation selected to up-regulate TK1 expression in the mammal may improve subsequent treatment by the pharmaceutical composition. Also, the pharmaceutical composition may be disposed in a suitable liquid carrier, such as one adapted for parenteral administration. One carrier may be or include isotonic saline or the like.

A method for diagnosing cancer in a human may include obtaining a sample of cells from a human subject and incubating the sample with at least a fragment of an anti-TK1 antibody. One may then detect an amount of antibody-TK1 complex in the sample. Quantifying a concentration of TK1 in the sample may be done by comparing the detected amount of antibody-TK1 complex with a standard curve generated using known amounts of TK1. The presence of cancer in the subject may then be diagnosed based on the concentration found.

One method in accordance with the invention may include determining the location and spread of neoplastic tissue in a patient. Administering a labeled TK1 antibody to a patient, it is then possible to visualize the labeled TK1 antibody. Determining the location and extent of spreading of neoplastic tissue in the patient corresponding to the visualized, labeled TK1 antibody, good tissues may be avoided in any treatment. For example, in a surgical procedure a physician may thus visually differentiate neoplastic tissue from normal tissue. Visualization may be accomplished by PET, MRI, CT, SPECT, the human eye unaided, or the like.

Labeling the TK1 antibody may be done with a dye, such as, for example, a fluorescent, radioactive, radio-opaque, or combination material. Also in embodiments where the anti-TK1 antibody recognizes and binds surface TK1 on cancer cells, it thereby marks and differentiates cancer cells from normal cells. This enables treatments to minimize removal of, or damage to healthy, normal tissue.

In some embodiments of methods in accordance with the invention, administering an anti-TK1 monoclonal antibody may target and destroy tumor cells that express TK1 on the surface thereof. The antibody may be introduced into the bloodstream of a mammal to bind to TK1 on the surface of cells. The treatment effect may be complement mediated lysis, antibody dependent cell mediated cell cytotoxicity, and apoptosis, a combination thereof, or the like, of targeted tumor cells.

In some embodiments an anti-TK1 monoclonal antibody coupled with anti-tumor agents may enhance the cytotoxic effects thereof, thereby killing substantially more tumor cells than normal cells. Administering anti-TK1 may also serve to inhibit an elevated level of TK1 enzyme activity, thereby decreasing cellular proliferation and slowing the spread of a disease.

A kit for treating mammals to inhibit, locate or destroy TK1 may include a suitable monoclonal anti-TK1 antibody and a device for delivering the antibody to a mammal. The device may include a container, a control, an output port, a septum, or any combination thereof. A syringe or suitable measurement or administration implement may or may not be included in the kit. Typically, instructions for use and care of the antibody may be included along with packaging to effect protection during transport and storage of the kit. Some kits may serve in locating, inhibiting, destroying, and reducing cellular proliferation of TK1, or a combination thereof. Anti-TK1 antibody or a fragment thereof may be bound to therapeutic substrates effective to accomplish one or more of the foregoing.

Further aspects, features and advantages of this invention will become apparent from the following detailed description of various embodiments of methods and apparatus in accordance with the invention.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 13 is a photograph of a microscope slide of normal (i.e., negative control) human lymphocytes stained with Oncoprev antibody using fluorescence microscopy at 100× no staining is observed;

FIG. 14 is a photograph of a microscope slide of normal human lymphocytes stained with Oncoprev antibody using fluorescence microscopy at 500× no staining is observed;

FIG. 15 is a photograph of a microscope slide of normal human lymphocytes stained with Oncoprev antibody using light microscopy at 100× verifying the presence of normal cells;

FIG. 16 is a photograph of a microscope slide of normal human lymphocytes stained with Oncoprev antibody using light microscopy at 100× verifying the presence of normal cells;

FIG. 36 is a chart from a standard report of results from a xenograft study of human colon cancer introduced into nude mice, showing the ability of a method in accordance with the invention to reduce growth of cancerous tumors;

FIG. 37 is a chart from a standard report of results from a xenograft study of human breast cancer introduced into nude mice, showing the ability of a method in accordance with the invention to reduce growth of cancerous tumors;

FIG. 38 is a chart showing an absence of TK1 on the surface of normal cells in every type of tissue in the human body;

FIG. 43 is a chart showing an example of data of staining demonstrating TK1 binding to solid tumor tissue;

DETAILED DESCRIPTION OF THE PREFERRED EMBODIMENTS

Figure 1:
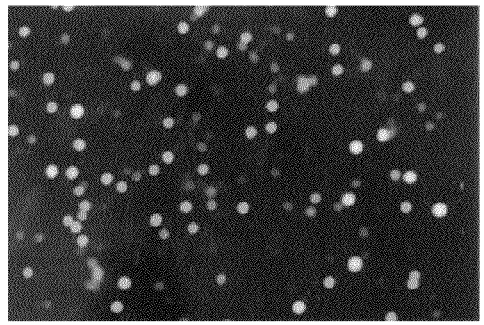
FIG. 1 is a photograph of a microscope slide of Burkitt's lymphoma (cancerous B cells) stained with Oncoprev Ab at 100× magnification.
Figure 2:
FIG. 2 is a photograph of a microscope slide of Burkitt's lymphoma (cancerous B cells) stained with Oncoprev Ab at 500× magnification.
Figure 3:
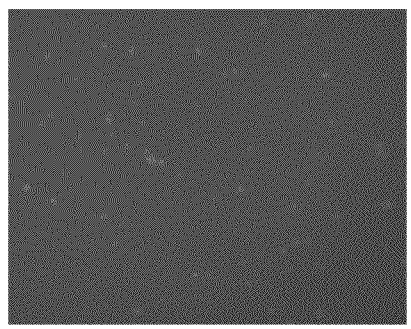
FIG. 3 is a photograph of a microscope slide of breast cancer cell line (MD-MBA-435) stained with Oncoprev Ab at 100× magnification.
Figure 4:
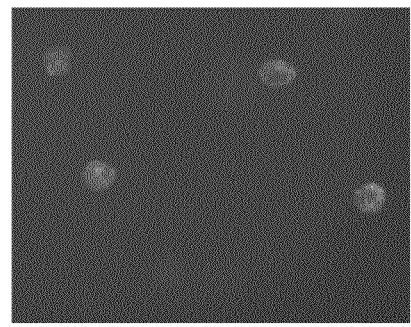
FIG. 4 is a photograph of a microscope slide of breast cancer cell line (MD-MBA-435) stained with Oncoprev Ab at 400× magnification.
Figure 5:
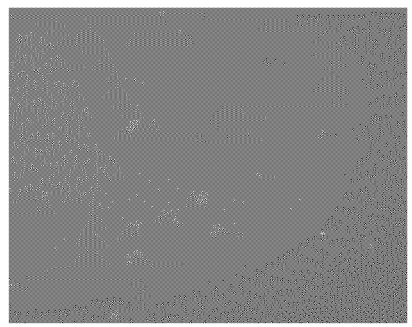
FIG. 5 is a photograph of a microscope slide of pancreatic cancer cells (PANC-1) stained with Oncoprev antibody at 100× magnification.
Figure 6:
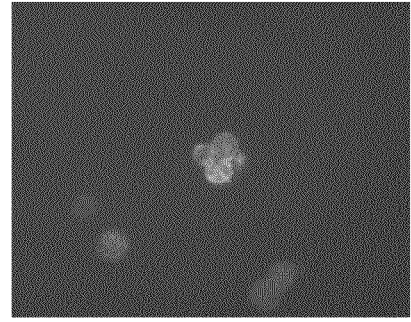
FIG. 6 is a photograph of a microscope slide of pancreatic cancer cells (PANC-1) stained with Oncoprev antibody at 400× magnification.
Figure 7:
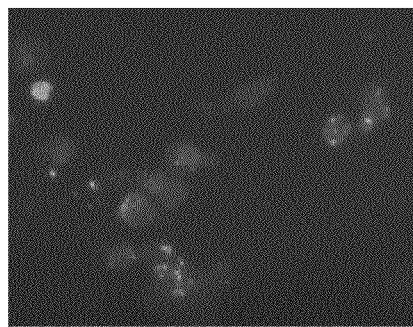
FIG. 7 is a photograph of a microscope slide of breast cancer cell line (MD-MBA-231 cells) stained with Oncoprev Ab at 400× magnification.
Figure 8:
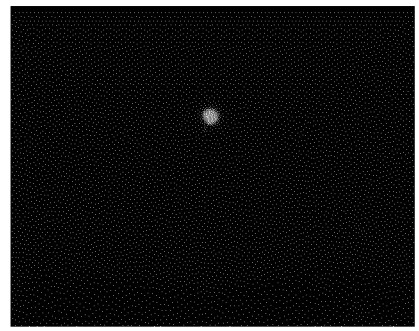
FIG. 8 is a photograph of a microscope slide of liver cancer cell line (Hep-G2) stained with Oncoprev antibody at 400× magnification (far fewer cells in the field)
Figure 9:
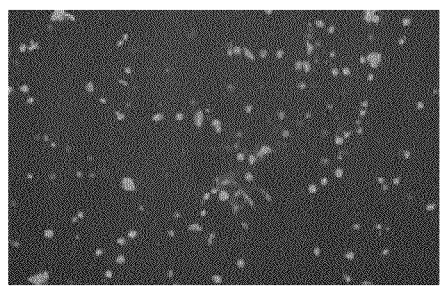
FIG. 9 is a photograph of a microscope slide of cervical cancer cell line (HELA cells) stained with Oncoprev antibody at 100×.
Figure 10:
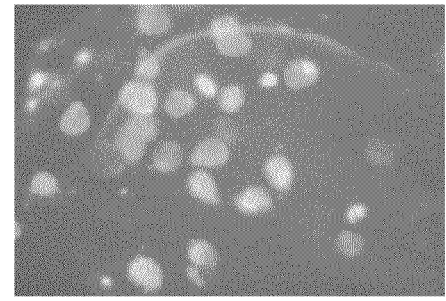
FIG. 10 is a photograph of a microscope slide of cervical cancer cell line (HELA cells) stained with Oncoprev antibody at 400×.
Figure 11:
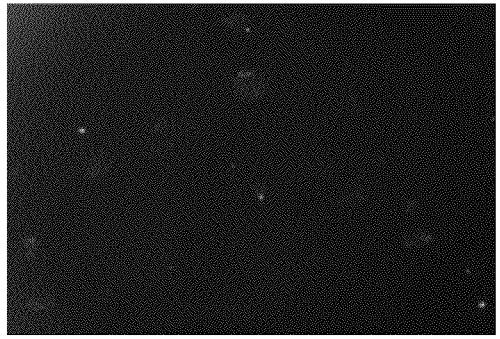
FIG. 11 is a photograph of a microscope slide of breast cancer cell line (MCF-7) stained with Oncoprev antibody at 100×.
Figure 12:
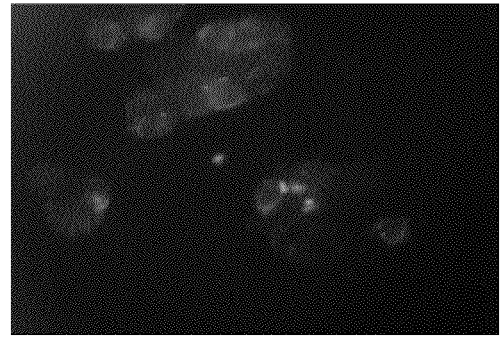
FIG. 12 is a photograph of a microscope slide of breast cancer cell line (MCF-7) stained with Oncoprev antibody at 400×.
Figure 17:
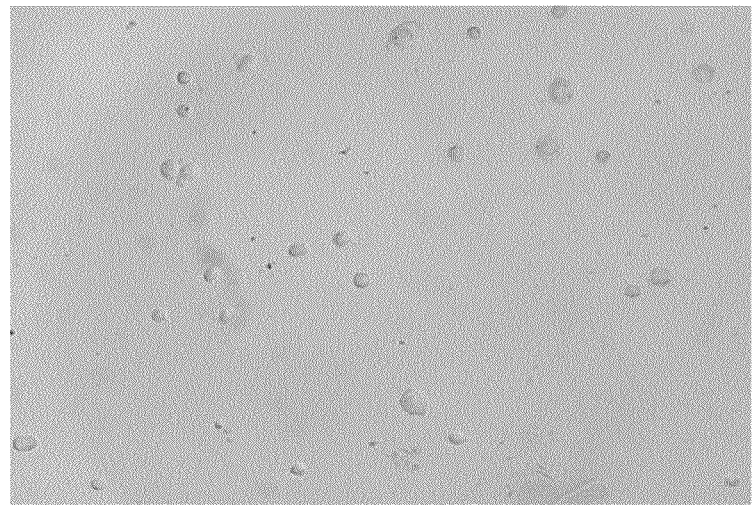
FIG. 17 is a photograph of a microscope slide of normal human fibroblasts stained with Oncoprev antibody using light microscopy at 100× verifying the presence of cells.
Figure 18:
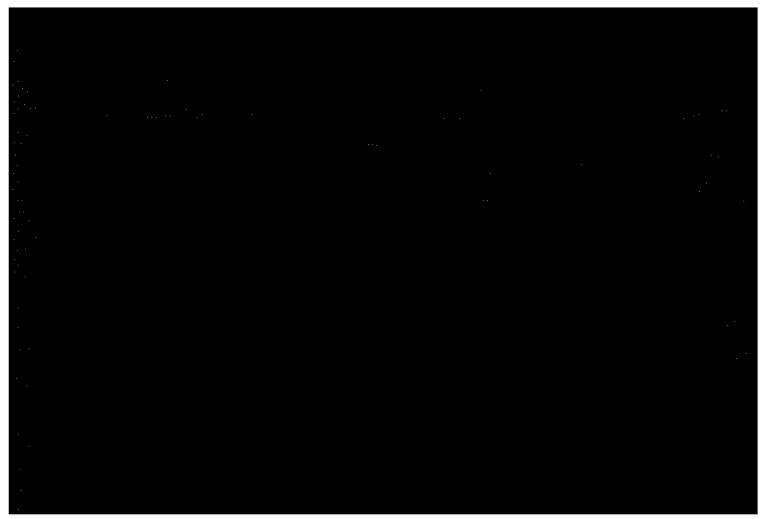
FIG. 18 is a photograph of a microscope slide of normal human fibroblasts stained with Oncoprev antibody using fluorescence microscopy at 100× showing no antibody because no staining is observed.
Figure 19:
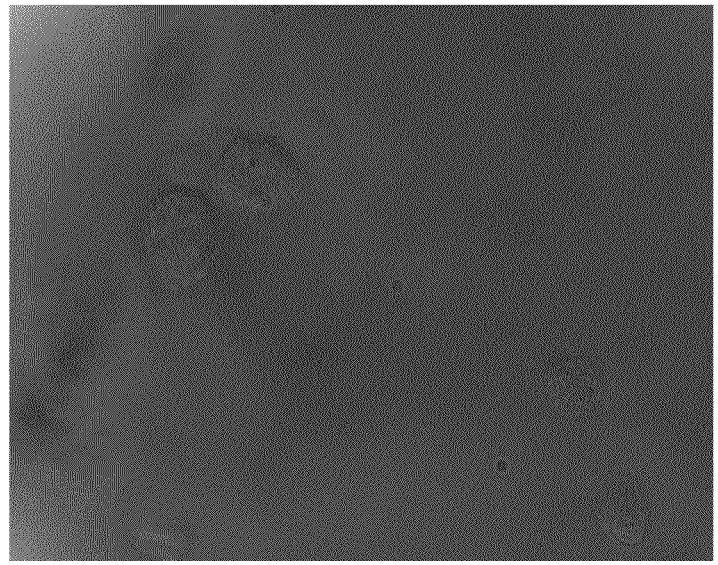
FIG. 19 is a photograph of a microscope slide of normal human fibroblasts stained with Oncoprev antibody using light microscopy at 400× verifying the presence of cells.
Figure 20:
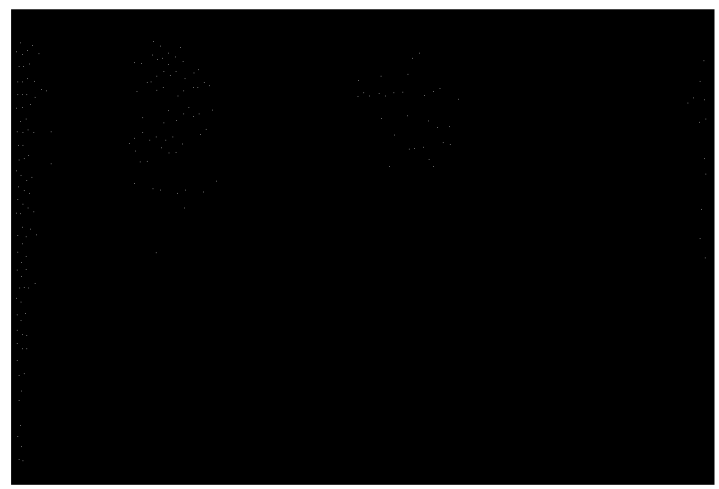
FIG. 20 is a photograph of a microscope slide of normal human fibroblasts stained with Oncoprev antibody using fluorescence microscopy at 400× showing an absence of antibodies, since no staining is observed.
Figure 21:
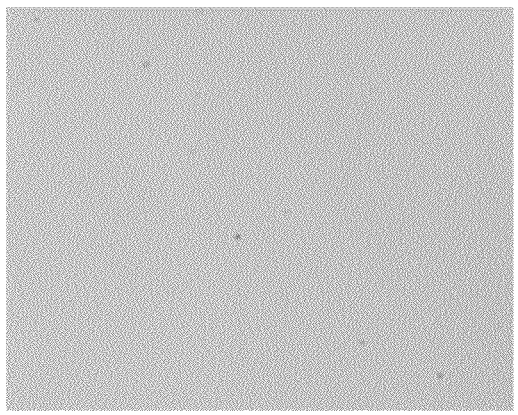
FIG. 21 is a photograph of a microscope slide of human lymphocytes using CB101 IgM antibody without serum.
Figure 22:
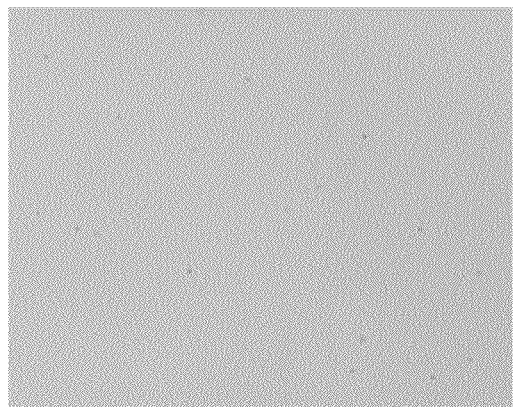
FIG. 22 is a photograph of a microscope slide of human lymphocytes with CB101 IgM antibody with serum showing no measurable lysis.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

While the described embodiments herein below represent illustrative embodiments in accordance with the present invention, it is to be understood that modifications will occur to those skilled in the art without departing from the spirit of the invention. The scope of the invention is therefore to be determined solely by the appended claims.

The following definitions are provided in order to provide clarity as to usage in the specification and claims.

The term "mammalian thymidine kinase 1 or TK1" as used herein refers to an enzymatically active TK1. In preferred modes, the TK1 is isolated and purified from a mammal, including, but not limited to, a mammalian body organ, tissue, cell, fluid or the like, in either normal or diseased condition, and presented as a fresh or preserved specimen, a cell tissue culture, a cell line, a hybridoma, or the like. Alternatively, the mammalian TK1 may be produced in host cells, preferably mammalian host cells, which have been engineered to contain a polynucleotide sequence that encodes TK1. In one embodiment, the polynucleotide encoding the TK1 is operably linked to an inducible promoter. The purified TK1 suitable for use in accordance with the invention, whether isolated from tissues or cells, or produced by recombinant DNA methods, provides a yield of purified TK1 sufficient for the preparation of antibodies to TK1.

The term "mammalian" as used herein refers to a human or other animal classified as a mammal.

The term "body fluid" as used herein refers to any fluid obtained from a mammal, for example, blood, serum, urine, spinal fluid, tears, or the like.

The term "body tissue" as used herein refers to any normal or diseased tissue obtained from a mammal, for example, organ tissue, biopsy tissue, tumors, or the like. A body tissue may be presented as a fresh or preserved (e.g., frozen) sample, a histological slide preparation, or the like.

The terms "antibody" and "immunoglobulin" are used generally to include polyclonal and monoclonal antibodies, and fragments thereof exhibiting the desired binding specificity and affinity, regardless of the source or immunoglobulin type (i.e., IgG, IgE, IgM, or the like) and so forth. The term "antibody to TK1", "TK1 antibody" or "anti-TK1 antibody" as used herein refers to an antibody or fragment thereof that binds to TK1.

The term "monoclonal antibody" is used in accordance with its ordinary meaning to denote a homogenous immunoglobulin resulting from the proliferation of a single clone of cells (e.g., hybridoma cells, eukaryotic host cells transfected with DNA encoding the homogenous immunoglobulin, prokaryotic host cells transformed with DNA encoding the homogenous immunoglobulin, or the like), and which is generally characterized by heavy chains of a single class and subclass, and light chains of a single type. It is contemplated that in some applications a polyclonal antibody to a purified TK1 of the instant invention can be utilized in place of an anti-TK1 monoclonal antibody of the invention. Note that not all TK1 antibodies inhibit the TK1 enzymatic activity because not all epitopes are at the catalytic site. Some antibodies were obtained that bound to TK1 but did not inhibit the TK1 enzymatic activity.

The term "therapeutic application" as used herein refers to any use of TK1, anti-TK1 monoclonal antibodies, or anti-TK1 polyclonal antibodies to target diseased tissues, wherein the diseased tissues are targeted, visualized, decreased, eliminated, or otherwise controlled as desired. It is contemplated that the therapeutic applications of this invention may be used in conjunction with or in isolation from other therapeutic applications now known or yet to be discovered.

The term "biotherapeutic agent" is used in its ordinary sense and to include the use of a MAb, pharmaceutical, protein or peptide, nucleic acid, or the like to treat or prevent disease or other abnormality in a mammal such as a human.

The term "complement mediated lysis" or CDC as used herein refers to a system of serum proteins activated by antibody-antigen complexes or by microorganisms, that helps eliminate selected microorganisms or cells by directly causing their lysis or by promoting their phagocytosis.

The term "Antibody-Dependent Cell-Mediated Cytotoxicity" (ADCC) as used herein refers to a mechanism of cell-mediated immunity whereby an effector cell of the immune system actively lyses a target cell that has been bound by specific antibodies. It is one of the mechanisms through which antibodies, as part of the humoral immune response, can act to limit and contain infection. Classical ADCC is mediated by natural killer (NK) cells; monocytes and eosinophils can also mediate ADCC.

The Term "Apoptosis" as used herein refers to a form of cell death in which a programmed sequence of events leads to the elimination of cells without releasing harmful substances into the surrounding area. Apoptosis plays a crucial role in developing and maintaining health by eliminating old cells, unnecessary cells, and unhealthy cells. The human body replaces perhaps a million cells a second. Too little or too much apoptosis plays a role in a great many diseases. When programmed cell death does not operate properly, cells that should be eliminated may persist and may even become "immortal". For example, in cancer and leukemia.

The terms "humanized immunoglobulin" or "humanized antibody" are used in their ordinary meanings and include any immunoglobulin or antibody or fragment thereof, produced at least partly in a non-human mammal, wherein at least one portion is of human origin.

The following described embodiments for the methods of production and use of anti-TK1 are to be considered in all respects only as illustrative and not restrictive. In certain embodiments of methods and processes in accordance with the current invention, production of various antibodies includes antibodies specific to active TK1, inactive TK1, multimeric TK1, and monomeric TK1. Additionally, the production may include various anti-TK1 antibodies specific to various TK1 epitopes. Consequently, the scope of this disclosure should not be read to limit the invention to a finite number of antibodies or to a finite number of epitopes on TK1.

The present inventor has found that, contrary to conventional wisdom, TK1 is expressed on the surface of cancer cells and virally-infected cells, not internally as in normal cells. TK1 expression is increased 6-30 times during cellular transformation or infection of mammalian cells. This observation is utilized in methods disclosed herein for treating cancer cells with an antibody to thymidine kinase. Methods based upon the observed mechanism pertaining to the treatment of proliferating (e.g., cancer) cells are disclosed in co-pending U.S. patent application Ser. No. 11/134,854, incorporated herein by reference.

It has been reported that in the presence of ATP, native TK1 shifts to a form of TK1 having a higher molecular weight, for example, human placental TK1 of 50 kD shifts to 70 kD in the presence of ATP and human lymphocytic TK1 of 55 kD shifts in the presence of ATP to a form having a molecular weight of 110 kD.

Not only are widely divergent values reported for the molecular weight of the native TK1, different views exist for the monomeric subunit of TK1. Molecular weights of 44 and 22-24 kD have been reported for the TK1 monomer. Further, reports vary as to whether the monomeric subunit is associated with TK1 enzymatic activity. For example, TK1 enzyme activity has been reported to be associated with the monomeric subunit of approximately 24 kD for the HeLa cells, rat liver, and human lymphocytes, but enzyme activity was not found associated with the monomeric subunit in the presence or absence of ATP for human placenta TK1.

Balis et al. (U.S. Pat. No. 4,317,877, Mar. 2, 1982) disclosed immune sera to a small subunit component of (a) TK from normal colonic mucosa and (b) TK from term human placenta. Although both small subunit components were electrophoretically similar, they were not antigenically identical as indicated by differences in precipitin patterns. Moreover, it was stated that "The lack of complete neutralization by these antisera of their respective homologous enzymes is not unexpected since only the small molecular weight component is used as antigen." Thus, it is considered that an antiserum to a subunit component of TK1 does not completely react with nor neutralize the active multimeric form of the TK1. Also, the Balis antibody did not react with leukemic leukocytes or with normal or mitogen-stimulated peripheral lymphocytes, even though these are known to have elevated TK levels.

U.S. Pat. No. 5,698,409, issued Dec. 16, 1997 (the '409 patent), which is incorporated herein by reference, describes a purified mammalian thymidine kinase 1 (TK1) from Raji cells and a TK1 monoclonal antibody. Raji cells are an immortalized human lymphoma cell line, available from ATCC as cell line #CCL-86. The 409 patent also describes a monoclonal antibody to TK1 which not only binds to TK1 but also inhibits TK1 activity.

TK-1 is a cellular enzyme involved in a "salvage pathway" of DNA synthesis. In normal growing cells thymidine kinase 1 mRNA rises near the G1-S boundary, peaks in early S phase, and returns in G2 to approximately the level of early G1. It is activated in the G1/S phase of the cell cycle, and its activity correlates with the proliferative activity of tumor cells. Proliferating cells appear to have lost the strict regulation of TK1 that is observed in normal cells. TK activity is a major biochemical marker of cell proliferation and several studies show that TK levels are elevated in malignancies including breast cancer, cervical cancer, colon cancer, liver cancer, lung cancer, melanoma, pancreatic cancer and T-cell lymphoma.

In DNA tumor virus-transformed cells, the level of TK mRNA remains relatively constant throughout all phases of the cell cycle. DNA tumor viruses may suppress a transcriptional down-regulation common to enzymes responsible for the DNA precursor pathway. In virally transformed cells lines both TK1 mRNA levels and TK1 activity remain elevated throughout the cell cycle (Different regulation of thymidine kinase during the cell cycle of normal versus DNA tumor virus-transformed cells).

The step catalysed by thymidine kinase 1 is the bottle neck of the S-phase gene pathway and is therefore rate limiting. Even slow-growing cancers or latent viral infections constitutively express TK1 on the cell surface making them susceptible to ADCC and CDC and apoptosis (A common regulation of genes encoding enzymes of the deoxynucleotide metabolism is lost after neoplastic transformation.

It has been demonstrated that TK1 mRNA and protein are up-regulated and constitutively expressed in cancer cells and virally-infected and virally-transformed cells (HSV-1, HSV-2, varicella-zoster virus (VZV), vaccinia virus, vesicular stomatitis, cytomegalovirus (CMV), and human immunodeficiency (HIV-1, HIV-2)). This occurs because most viruses force cells to manufacture the enzymes required for DNA synthesis so the viruses can generate sufficient nucleotides for viral replication or, in the case of retroviruses, for integration into the host genome. DNA tumor viruses suppress transcriptional down-regulation of the endogenous DNA precursor pathway enzyme TK1 during the eukaryotic cell cycle to improve conditions for their own replication. TK levels are not detectable in quiescent cells.

In one method in accordance with the invention, cancer cells are selectively targeted by TK1 antibody and killed via complement dependent lysis (CDC) or antibody dependent cellular cytotoxicity (ADCC), or by apoptosis. Such processes are initiated by treating patients with anti-TK1.

In some embodiments, the cytotoxicity of TK1 antibody may be enhanced by first treating patients with radiation therapy, in order to up-regulate TK1 expression. The DNA damage requires the generation of new nucleotides for DNA repair, resulting in more TK1 expressed. After up-regulation of TK1 expression, the patient is treated with the TK1 antibody, which binds the TK1 on the cell surface. By focusing the radiation therapy the toxicity of the antibody—if any—can be limited to the site of the tumor.

Embodiments in accordance with the present invention provide a biotherapeutic agent, a monoclonal antibody to TK1. In some embodiments, the biotherapeutic agent may be an immunoconjugate or immunotoxin, that includes a monoclonal antibody specific to TK1, linked to an effective amount of moiety, e.g., a polypeptide or a toxin having biological activity.

Examples of useful biologically active moieties include ricin A chain immunotoxin, saporin, gelonin, *Pseudomonas* exotoxin, Pokeweed anti-cancer protein, or an active fragment of one of the foregoing. The activity of a preparation of pokeweed anti-cancer protein can be determined by methods in U.S. Pat. No. 6,372,217 incorporated herein by reference. However, it is emphasized that it is not necessary in all embodiments to conjugate TK1 to an immunotoxin. The monoclonal antibody to TK1 alone may be pharmaceutically active.

In one embodiment the anti-TK1 biotherapeutic agent of the present invention employs the monoclonal antibody TK1 or a biologically active subunit, fragment or derivative thereof, which binds to TK1 present at the surface of virally-infected cells. A "biologically active" subunit or fragment of a monoclonal antibody has at least about 1% of the binding activity of the monoclonal antibody. The antibody is even more effective if it has at least about 10% of the binding activity. Even better is at least about 50 of the binding activity of the monoclonal antibody.

The present invention provides a method to treat cancer and to inhibit cancer cellular replication in mammalian cells. The method comprises treating mammalian cells in vivo or treating a mammal having, or being at risk of, cancer by administering an effective amount of either an antibody to TK1 or an immunoconjugate that includes an antibody to TK1. Moreover, the present TK antibody or TK1-immunojugate may also provide the basis for an effective method to inhibit cancers including, but not limited to all known cancer types as shown by testing reported herein. Methods are also disclosed herein for detection of increased expression of TK1 in a patient sample, which indicates to the diagnostician the probability of the presence of cancer. The results of these assays are used for further testing to provide a disease diagnosis.

In some embodiments, the anti-TK1 biotherapeutic agent is used in combination with a second anti-cancer agent. The anti-cancer agent may be a chemotherapy, another monoclonal antibody or radiation therapy.

Monoclonal antibodies (MAbs) are produced in accordance with one embodiment of the present invention by the fusion of spleen lymphocytes with malignant cells (myelomas) of bone marrow primary tumors. The procedure yields a hybrid cell line, or hybridoma, arising from a single fused cell hybrid, or clone, which possesses characteristics of both the lymphocytes and myeloma cell lines. Like the lymphocytes (taken from animals primed with sheep red blood cells as antigens), the fused hybrids or hybridomas secrete antibodies (immunoglobulins) reactive with the antigen.

Moreover, like the myeloma cell lines, the hybrid cell lines are immortal. Specifically, whereas antisera derived from vaccinated animals are variable mixtures of antibodies which cannot be identically reproduced, the single-type of immunoglobulin secreted by a hybridoma is specific to one and only one determinant on the antigen, a complex molecule having a multiplicity of antigenic molecular substructures, or determinants (epitopes). Hence, monoclonal antibodies raised against a single antigen may be distinct from each other, depending on the determinant that induced their formation.

However, all of the antibodies produced by a given clone are identical. Furthermore, hybridoma cell lines can be reproduced indefinitely, are easily propagated in vitro and in vivo, and can yield monoclonal antibodies in extremely high concentrations.

Monoclonal antibodies have largely been applied clinically to the diagnosis and therapy of cancer, the modulation of the immune response to produce immunosuppression for treatment of autoimmune and graft versus host diseases (GVHD), and for prevention of allograft rejection. Human monoclonal antibodies have also been applied clinically against cytomegalovirus, Varicella zoster virus, and the various specific serotypes of *Pseudomonas aeruginosa, Escherichia coli*, and *Klebsiella pneumoniae*.

Some monoclonal antibodies useful in the present invention are produced using well known hybridoma fusion techniques. As indicated above, in one embodiment the present invention uses a monoclonal antibody directed against TK1.

U.S. Pat. No. 5,698,409 describes a purified mammalian thymidine kinase 1 (TK1) from Raji cells. Raji cells are an immortalized human lymphoma cell line, available from ATCC as cell line #CCL-86. U.S. Pat. No. 5,698,409 also describes a monoclonal antibody to TK1 which not only binds to TK1 but also inhibits TK1 activity. Specific anti-TK1 antibody monoclonal producing hybridomas are available as ATCC HB 11432, HB 11433 and HB 11434.

Some embodiments rely on a humanized anti-TK1 MAb. The humanized antibody can comprise portions derived from an immunoglobulin of nonhuman origin with the requisite specificity, such as a mouse, and from immunoglobulin sequences of human origin (e.g., a chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain).

Another example of a humanized immunoglobulin in accordance with the present invention is an immunoglobulin containing one or more immunoglobulin chains comprising a CDR of nonhuman origin (e.g., one or more CDRs derived from an antibody of nonhuman origin) and a framework region derived from a light, heavy, or both, chain of human origin (e.g., CDR-grafted antibodies with or without framework changes). Chimeric or CDR-grafted single chain antibodies are also encompassed by the term humanized immunoglobulin.

Also included within the scope of the invention are humanized antibodies which have been veneered or reshaped. For example, the rodent variable region is compared to the consensus sequence of the protein sequence subgroup to which it belongs, and the selected human constant region accepting framework is compared with its family consensus sequence. Idiosyncratic residues are replaced by more commonly occurring human residues.

Such humanized immunoglobulins can be produced using synthetic and/or recombinant, or both, nucleic acids to prepare genes encoding the desired humanized chain. For example, in U.S. Pat. No. 4,816,567 (incorporated herein in its entirety by reference) altered and native immunoglobulins, including constant-variable region chimeras, may be prepared in recombinant cell culture. The immunoglobulins contain variable regions which are immunologically capable of binding predetermined antigens. Methods may be used for refolding directly expressed immunoglobulins into immunologically active form (See also, U.S. Pat. No. 6,331,415; incorporated in its entirety by reference). In other examples, nucleic acid sequences coding for humanized variable regions can be constructed using PCR mutagenesis methods to alter DNA sequences encoding a human or humanized chain, such as a DNA template from a previously humanized variable region. Using these or other suitable methods, variants can also be readily produced. In one embodiment, cloned variable regions can be mutagenized, and sequences encoding variants with the desired specificity can be selected (e.g., from a phage library.)

Alternatively, humanized antibodies may be conveniently prepared by injection of purified TK1 into SKID mice or other SKID animals that have accepted xenografts of adult human peripheral blood leukocytes as described in U.S. Pat. No. 5,476,996, which is incorporated herein by reference in its entirety. By this treatment, human immune function is introduced into the SKID animal which can be used to produce humanized antibodies.

Immunotoxins

Certain embodiments of methods in accordance with the invention include the use of an immunotoxin linked to the anti-TK1 MAb. Several requirements must be fulfilled for an immunotoxin to be effective. First of all, the immunotoxin should be specific and should not react with tissues that do not express the target antigen to the extent that such is detrimental to the target mammal. Binding to tissues that do not express the antigen can be reduced by removal of the nonspecific, natural, cell-binding subunits or domains of the biotherapeutic moiety, e.g., a plant glycoprotein toxin or anti-cancer agent.

Furthermore, plant glycoprotein toxins contain mannose oligosaccharides that bind to cells of the reticuloendothelial system. In some cases, they also contain fucose residues that are recognized by the receptors on hepatocytes. Thus, deglycosylation of plant toxins may be required to avoid rapid clearance and potential cytotoxic effects on these cells.

Secondly, the linkage of the toxin to the antibody should not substantially impair the capacity of the antibody to bind to the antigen. Third, the immunotoxin must be effectively internalized into the endosomic vesicles. Thus, toxins directed by monoclonal antibodies to surface receptors that are otherwise normally internalized may be more active than those directed toward noninternalizing cell surface molecules.

Fourth, the active component of the toxin must translocate into the cytoplasm. Finally, for in vivo therapy, the linkage between the MAb and the toxin must be sufficiently stable to remain intact while the immunotoxin passes through the tissues of the mammal to its cellular site of action.

The activity of an immunotoxin is initially assessed by measuring its ability to kill cells with target antigens on their surfaces. Because toxins act within the cells, receptors and other surface proteins that naturally enter cells by endocytosis are usually appropriate targets for immunotoxins. Surface proteins fixed on the cell surface are typically not.

However, if several antibodies recognizing different epitopes on the same cell surface protein are available, it is useful to test them all. This is because some antibodies, perhaps by producing a conformational change in the target protein, may more efficiently induce internalization or direct intracellular routing to an appropriate location for toxin translocation.

Also, if the receptors are efficiently internalized, it is possible to employ an immunotoxin that does not bind as strongly to the receptor. This is due to the chemical modification(s) needed to prepare the immunotoxin. Willingham et al., Proc. Natl. Acad. Sci. USA, 84, 2474 (1987).

Toxins

An array of toxins of bacterial and plant origin have been coupled to MAbs for production of immunotoxins. The strategy is to select from nature a cytotoxic protein and then to modify the cytotoxic protein so that it will no longer indiscriminately bind and kill normal cells. It will instead kill only the cells expressing the antigen bound by the MAb.

To be optimally effective, such an approach requires that internalization of relatively small numbers of cytotoxic molecules be lethal to target cells, as there are limited receptor sites on the cell surface for a given MAb. The toxins produced by certain bacteria and plants that inactivate cellular protein synthesis meet this criterion. Unlike most chemotherapeutic agents that act in a stoichiometric manner, they are catalytic in their lethal activity. In general, less than ten toxin molecules in the cytoplasm of a cell are sufficient to kill the cell.

Two classes of toxins that inactivate protein synthesis have been widely employed in the construction of immunotoxins. The first class consists of intact toxins, such as intact ricin. These toxins cannot be safely applied in vivo because of lethal toxicity.

The second group of toxins are referred to as hemitoxins. Lethally inhibiting protein synthesis in a complementary manner, hemitoxins covalently modify the ribosome such that it can no longer productively interact with elongation factor 2. This latter family of toxins includes pokeweed anti-cancer protein (PAP), ricin, abrin, gelonin, saporin, and alpha-sarcin.

The ribosome inactivating proteins derived from plants have either two chains, including a binding chain and catalytic chain (e.g., ricin), or a single catalytic chain alone (e.g., PAP or saporin).

In certain embodiments, anti-TK1 antibody immunotoxins for use in the present method are formed by linking an effective cytotoxic or anti-cancer amount of immunotoxin molecules to each molecule of anti-TK1 antibody. For example, a reagent useful in the practice of methods in accordance with the invention includes one to two immunotoxin molecules per anti-TK1 antibody molecule. An effective composition in accordance with the invention includes about a 1:1 mixture of a) one molecule of immunotoxin/molecule of anti-TK1 antibody, and b) two molecules of immunotoxin/molecule of anti-TK1 antibody. In one effective embodiment, a composition in accordance with the invention contains mainly 1 or 2 immunotoxin molecules per intact anti-TK1 monoclonal antibody molecule, free anti-TK1 monoclonal antibody, and free immunotoxin.

Modes of Administration of Anti-TK1 MAb or Anti-TK1 Antibody Biotherapeutic Agent An anti-TK1 MAb or anti-TK1 antibody biotherapeutic agent in accordance with the invention, or a combination thereof, may be formulated as a pharmaceutical composition and administered to a human or other mammal with cancer, typically as a unit dosage form comprising an effective amount of one or more of the anti-TK1 MAb or anti-TK1 antibody, optionally coupled to an immunotoxin. This may be administered in combination with a pharmaceutically acceptable carrier or vehicle, in combination with other therapeutic agents, or both.

Dosage Forms

The anti-TK1 MAb or anti-TK1 antibody biotherapeutic agent of the present invention may be parenterally administered, i.e., intravenously, or subcutaneously by infusion or injection. Solutions or suspensions of the biotherapeutic agent may be prepared in water, or a physiological salt solution such as isotonic saline or PBS, optionally mixed with a nontoxic surfactant.

Although the anti-TK1 MAb or anti-TK1 antibody biotherapeutic agent may typically be administered as a liquid composition as described herein, it may be administered with a variety of other carriers. For example, dispersions may also be prepared in glycerol, liquid polyethylene glycols, DMA, vegetable oils, triacetin, and mixtures thereof. Under ordinary conditions of storage and use, these preparations may contain a preservative to prevent the growth of microorganisms. Additionally, more specific delivery of the anti-TK1 MAb or anti-TK1 antibody biotherapeutic agent to the lungs may be accomplished via aerosol delivery systems.

The compositions suitable for injection or infusion may include sterile aqueous solutions or dispersions or sterile powders comprising the anti-TK1 MAb or anti-TK1 antibody biotherapeutic agent adapted for the extemporaneous preparation of sterile injectable or infusible solutions or dispersions. In all cases, the ultimate composition should be, and typically must be sterile, fluid and stable under the conditions of manufacture and storage.

The liquid carrier or vehicle may be a solvent or liquid dispersion medium comprising, for example, water, ethanol, a polyol (for example, glycerol, propylene glycol, and liquid polyethylene glycols, and the like), vegetable oils, nontoxic glycerol esters, lipids (for example, dimyristoyl phosphatidyl choline) and suitable mixtures thereof. The proper fluidity may be maintained, for example, by the formation of liposomes, by the maintenance of the required particle size in the case of dispersion or by the use of nontoxic surfactants. The prevention of the action of microorganisms may be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions may be brought about by the inclusion in the compositions of agents delaying absorption, for example, aluminum monostearate hydrogels and gelatin.

Sterile injectable or infusable solutions may be prepared by incorporating the anti-TK1 MAb or anti-TK1 antibody biotherapeutic agent in the required amount in the appropriate solvent with various of the other ingredients enumerated above. As required, this may be followed by filter sterilization. In the case of sterile powders for the preparation of sterile injectable or infusable solutions, the typical methods of preparation are vacuum drying and the freeze drying techniques. These yield a powder of the active ingredient plus any additional desired ingredient present in the previously sterile-filtered solutions.

Furthermore, suitable formulations for the anti-TK1 MAb or anti-TK1 antibody biotherapeutic agent of the present invention may include those suitable for oral, rectal, nasal, topical (including, ocular, and sublingual) or vaginal administration or in a form suitable for administration by inhalation or insufflation. The formulations may be prepared by any suitable methods known in the art of pharmacy. Such methods may include the step of bringing into association the biotherapeutic agent with liquid carriers, finely divided solid carriers, or both and then, if necessary, shaping the product into the desired formulation.

Pharmaceutical formulations suitable for oral administration may conveniently be presented as discrete units such as capsules, sachets, or tablets, each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain any suitable additives, such as suspending agents, emulsifying agents, non-aqueous vehicles (which may include edible oils), or preservatives.

The biotherapeutic agent of the present invention may also be formulated for intra-nasal or ocular administration. In this form of administration, the active ingredient may be used as a liquid spray or dispersible powder or in the form of drops. Drops, for example, eyedrops, may be formulated with an aqueous or non-aqueous base also comprising one or more dispersing agents, solubilizing agents or suspending agents. Liquid sprays may be conveniently delivered from pressurized packs.

For administration by inhalation, the biotherapeutic agent is conveniently delivered from an insufflator, nebulizer, pressurized pack, or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the biotherapeutic agent may take the form of a dry powder composition, such as, for example, a powder mix of the compound or a suitable powder base such as lactose or starch. The powder composition may be presented in unit dosage form in, for example, capsules or cartridges (e.g., gelatin, blister packs, or the like) from which the powder may be administered with the aid of an inhaler of insufflator.

Additionally, the anti-TK1 MAb or anti-TK1 antibody biotherapeutic agent of the present invention is well suited to formulation in controlled release dosage forms. The formulations may be so constituted that they release the active dry ingredient only at or preferentially in a particular physiological location, optionally over a period of time. The coatings, envelopes, and protective matrices may be made, for example, from polymeric substances or waxes. The compounds may also be delivered via patches for transdermal delivery, subcutaneous implants, infusion pumps, or via release from implanted depot sustained release dosage forms.

Dosages

The dosage of the biotherapeutic agents in the compositions of the invention may be varied widely, in accord with the size, age, and condition of the mammal and the disease. Dosages may typically be administered with a frequency based on the plasma half life of anti-TK1 MAb or anti-TK1 antibody biotherapeutic agent in a given patient. Higher doses may be employed in some cases. The doses may readily be adjusted to provide appropriate amounts of the biotherapeutic agent to children.

Example 1

Production of Monoclonal Antibodies Binding to TK1

Hybridoma cell lines producing antibodies to TK1 were produced by methods generally known in the art. The method does not seem to be relevant nor does the epitope to which the antibody binds. Applicant has had success with antibodies to the carboxy terminal end of TK1, to the active site of TK1 and to other epitopes on TK1 of undetermined location. Antibodies may be made to partial proteins, purified TK1, or whole synthetic protein recombinants manufactured from the TK1 protein sequence, placed as vectors into bacteria and wheat and purified from the supernatant.

Example 2

Detection of Active TK1 in Samples from Cancer Patients Using Anti-TK1 Antibody

It has been established that TK activity is elevated in the serum of patients with different kinds of cancer. For the most part, sera of patients with cancer showed an elevated TK1 activity compared to control patients.

A similar correlation between serum TK1 values and the presence of cancer was obtained using anti-TK1 monoclonal antibodies for measurement of TK1. Serum samples were obtained from cancer patients. Each sample was assayed for TK activity by a method like that of Example 1. The same samples were then quantitated blindly on an ELISA test with Clone 1 antibody using different serum dilution levels. A dilution of 1:16,000 was found to give the best results. The data were confirmed by Western blot analysis.

It can be seen from the TK1 activity measurements that the correlation is excellent between antibody binding data and the standard TK1 activity assay. The data demonstrate that the anti-TK1 antibody can be used to evaluate the serum level of TK1 activity in human subjects. Further, serum from a healthy (non-cancer-bearing) individual bound much less anti-TK1 antibody as compared to the lowest-ranked serum of cancer patients. Thus, the anti-TK1 antibody is useful to distinguish between serum of cancer-bearing individuals and serum from healthy non-cancerous individuals.

Example 3

Diagnostic and Prognostic Tests Utilizing Anti-TK1 Antibodies

Additionally, this invention contemplates development of specific tests, which utilize anti-TK1 antibodies to diagnose the presence of cancer. An example of this embodiment is comprised of the use of IFA- and ELISA-based, non-invasive, monoclonal TK1 tests that indicate both early cancer onset and provide clinical prognosis during treatment. The widespread appearance of TK as an early cancer marker and the data suggesting its usefulness as a prognostic tool for the clinician signals an important development in obtaining higher cancer survival rates.

For example the invention contemplates an IFA based diagnostic test designed to detect TK1 in patient tissue samples and blood, using a fluorescent compound to detect the binding of antigen and antibody. The anti-TK1 antibody is labeled with the fluorescent compound and its presence is detected using a fluorescence microscope. This IFA test may be used to detect the presence and quantity of TK1 in the patient's tissue, which is matched against a standard curve to provide the clinician with diagnostic and prognostic information.

This example comprises the following steps. Techniques generally known in the art may be utilized to conduct all the following protocols. The patient sample is prepared, which is normally a tissue section, cytology smear, or impression smear from the patient but is not limited to these particular types of samples. The unknown sample is fixed to a slide. Fluorescent labeled anti-TK1 antibodies and the patient sample are combined to allow the antibody to bind to TK1 (if TK1 is present). Subsequently, the slides are washed to remove everything but the antibodies bound to TK1. After washing, antibody-antigen binding is detected by observing the slide under a fluorescence microscope. Samples testing positive of the antigen of interest, in this example TK1, fluoresce, while samples testing negative for the antigen of interest do not. The sample slide is then compared to a standard curve.

Additionally, this invention contemplates development of other specific tests that utilize anti-TK1 antibodies to diagnose the presence of cancer. An additional example of this embodiment uses an ELISA-based diagnostic test designed to detect TK1 in a patient's serum sample, which can be optimized to run on any standard plate reader. In the ELISA based diagnostic exam contemplated by this embodiment, the antigen being measured is TK1.

One of the methods comprises the following steps. An antibody that reacts with the TK1 is firmly attached to the surface of the microtiter plate. The patient serum sample being tested is added and incubated, which allows the antibodies on the plate to bind with TK1. The plate is then washed to remove everything but the TK1 bound to antibodies. A second antibody that reacts with another epitope on TK1 and that is covalently attached to an enzyme is added and incubated with the antibody-TK1 complex in the second step above. The plate is then washed again to remove everything but the TK1 bound to antibodies. A colorless substrate of the enzyme is added. If TK1 is present in the patient serum sample, the enzyme-linked antibodies will convert the colorless substrate to a colored product. The fluorescence of the plate is measured and compared to a standard curve.

Example 4

Cell Lines Utilized

In addition to the previously mentioned cell lines, the following cell lines were used throughout the development and testing of the Mabs for the purposes of the present invention: Raji (human Burkitt's lymphoma, American Type Culture Collection (ATCC) CCL 86), TK-6 (human lymphoblastoid, ATCC CCL 8015), WTK-1 (human lymphoblastoid, isolated from the WI-L2-NS cell line, ATCC CRL 8155), Molt-4 (human peripheral blood, acute lymphoblastic leukemia, ATCC CRL 1582), HL-60 (human promyelocytic leukemia ATCC CRL 240), HL-60R (human promyelocytic leukemia with mutated retinoic acid receptor—a gene obtained from Dr. Byron Murray, Brigham Young University), Jurkat (acute T-cell leukemia, ATCC TIB 152), MCF-7 (human breast adenocarcinoma, ATCC HTB 22), SP2/0-A14 (murine myeloma, ATCC CRL 8006), and HeLa (Cervix adenocarcinoma, ATCC CCL 2.1).

All lymphoma cell lines were maintained in exponential growth phase in RPMI-1640 medium supplemented with 10% fetal bovine serum (FBS). SP2/0-Ag14 murine myeloma cells and hybridoma cells were cultured in Dulbecco's modified Eagle's medium (DMEM) supplemented with 10% heat-inactivated FBS with 0.1 mM hypoxanthine, 4 3 1025 mM aminopterin, and 1.6 3 1022 thymidine (HAT) medium for selection and withdrawal of the HAT medium after selection.

Example 5

Immunofluorescence of Bound Anti-TK1 Antibodies

The ability of the Oncoprev™ and 14F2 MAbs to detect TK1 in cells by immunofluorescence techniques were investigated. In these experiments, cancer cells were incubated with Oncoprev™ and both Oncoprev™ stained positive for TK1 (FIGS. 1 through 12). Normal cells that divide exponentially growing cells were incubated with Oncoprev™ Cancer cells showed a high level of TK1 staining; however, normal cells, including lymphocytes did not stain indicating low levels of TK1 (FIGS. 13-20).

This further supported the observed specificity of the antibodies to TK1. Cell cycle progression was halted by serum starvation and verified using flow cell cytometry (data not shown). When serum was added to the medium, cells reentered the cell cycle at G1 and continued growing. After serum starvation, cells had very low TK1 activity as determined by the radioisotope assay (0.1532+0.0423 CPM/cell), while cells 14 h after reentering the cell cycle had high TK1 activity (1.1154+0.3580 CPM/cell). Thus, we found that cells with high human TK1 levels stained positive with MAbs Oncoprev™, whereas cells with very low TK1 activity stained negative.

Additional assays demonstrate that selected monoclonal antibodies bind specifically to cells producing TK1. Immunofluorescence was utilized to further characterize the ability of anti-TK1 antibodies to specifically target cancer cells. Techniques generally known in the art were utilized in to conduct all the aforementioned assays and plots. One of the methods followed to produce successful immunofluorescence assays comprises the following steps.

First, cancer cells were harvested in exponential growth phase, washed twice with PBS, and fixed in 2.0 mL of a solution containing 1 part glacial acetic acid: 3 parts methanol for 5 min on ice, the cells were dropped onto slides. Slides were then hydrated through a graded series of ethanol to water.

Following three additional washes in PBS, cells were incubated in 25 mg/mL of Oncoprev™ anti-TK1 Mab (isotype IgG2a, available from Abnova catalog number H00007083-M02) for 2 h at RT. Cells were again washed 3 times in PBS and incubated with FITC-conjugated sheep anti-mouse IgC (H1 L chains) followed by 3 additional washes in PBS. Cells were then mounted in a solution containing 50% glycerol and 0.5 M sodium bicarbonate at pH 9.5.

Immunofluorescence of the slides was visualized using a Zeiss Axioskop microscope (Zeiss, Thornwood, N.Y.) and photographed with Kodak film (Rochester, N.Y.). Control samples were incubated in PBS instead of anti-TK1 MAbs.

Figure 25:
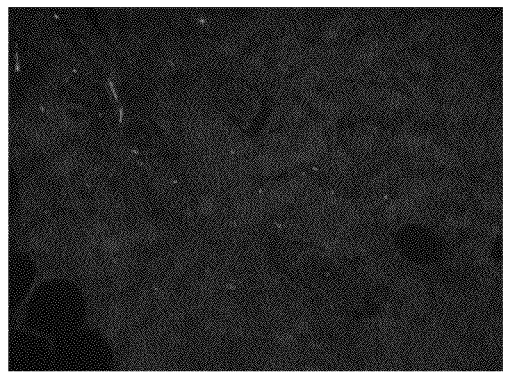
FIG. 25 is a photograph of a microscope slide of non-cancerous breast tissue stained with Oncoprev antibody showing the absence of TK1.
Figure 26:
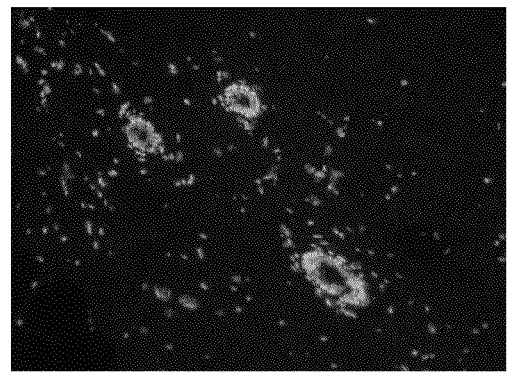
FIG. 26 is a photograph of a microscope slide of non-cancerous breast tissue (sequential to that of FIG. 25) stained with DAPI showing that normal dividing cells are stained.

FIG. 25 was produced using the aforementioned immunofluorescence techniques. Anti-TK1 monoclonal antibodies were used to stain non-cancerous, normal tissue. Breast and lymph node tissue was taken distally from a breast biopsy and was observed by pathologists via microscopy. A pathologist determined the tissue to be non-cancerous. The slide was visualized utilizing the immunofluorescence protocol previously discussed. FIG. 25 shows no anti-TK1 monoclonal antibody staining. This result demonstrates that anti-TK1 antibodies will not bind to healthy tissues.

Figure 27:
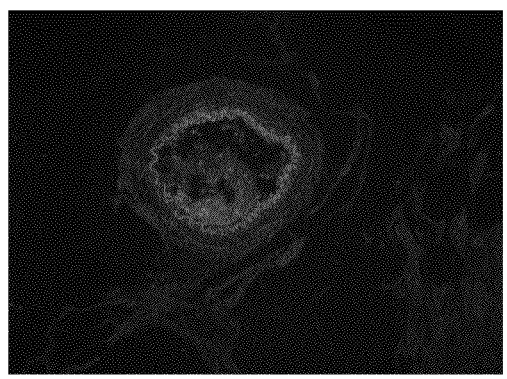
FIG. 27 is a photograph of a microscope slide of breast cancer tissue stained with Oncoprev antibody lighting up only the cancerous duct area.
Figure 28:
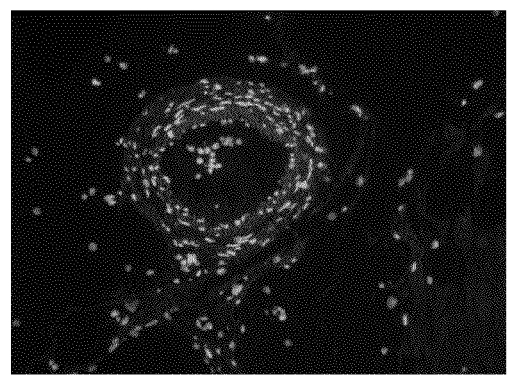
FIG. 28 is a photograph of a microscope slide of breast cancer tissue (sequential to that of FIG. 27) stained with DAPI lighting up the cancerous duct area AND normal cells.
Figure 29:
FIG. 29 is a photograph of a microscope slide of breast cancer tissue stained with Oncoprev antibody lighting up only the cancerous duct area.
Figure 30:
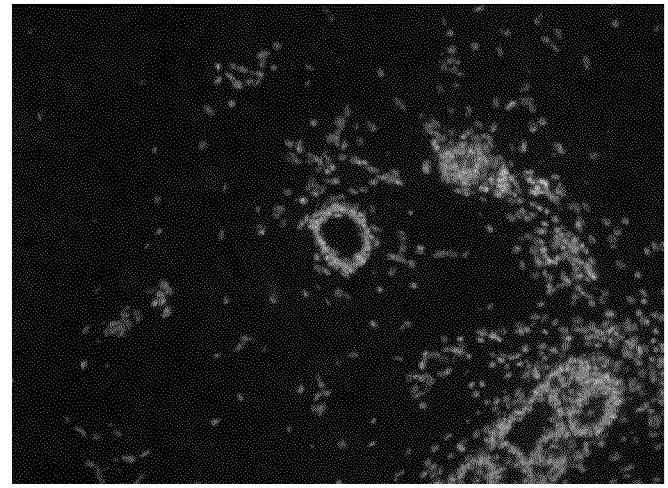
FIG. 30 is a photograph of a microscope slide of breast cancer tissue (sequential to that of FIG. 29) stained with DAPI lighting up the cancerous duct area and normal cells in the process of dividing (i.e., having open stranded DNA)

FIGS. 27, 29 are another example where anti-TK1 monoclonal antibodies were used to stain cancerous tissue utilizing the aforementioned technique. FIGS. 27, 29 are a visualization of stage II ductal cell carcinoma of the breast, stained with anti-TK1 monoclonal antibodies. Dark staining shows the presence of tumor tissue. FIGS. 27, 29 indicate that monoclonal anti-TK1 antibodies are binding specifically to cancerous tissues but not to healthy non-cancerous tissues as previously indicated in FIG. 25.

Additionally, none of the healthy tissues surrounding the cancerous tissue was stained. Thus the boundaries of the cancerous cells are clearly defined, cancerous cells being targeted by the monoclonal antibodies and the healthy tissues remaining unstained. Thus, the combined examples of FIGS. 1-12 and FIGS. 13-20 indicate that anti-TK1 antibodies bind cancerous tissues but not to healthy tissues.

Example 6

Immunohistochemical Detection of TK1 in Cells

Additional assays demonstrate that selected monoclonal antibodies bind specifically to cells producing TK1. Immunohistochemistry was utilized to further characterize the ability of anti-TK1 antibodies to specifically target cancer cells. Techniques generally known in the art were utilized in the various Immunohistochemistry assays performed. One of the methods followed comprises the following steps. TK-6 cells were serum starved for 24 h to induce growth arrest followed by stimulation with fresh RPMI 1640 medium supplemented with 10% FBS. Cells were then harvested at 0 and 14 hours following serum starvation and washed 3 times with PBS. Then, these cells were fixed as described in by the techniques previously described in "Immunofluorescence."

Endogenous peroxidase activity was neutralized with 0.6% H2O2 for 15 min. Slides were incubated with 10 mg/mL purified anti-TK1 MAb from either clone Oncoprev™ for 1 hour at RT. Bound antibodies were visualized with horseradish peroxidase labeled secondary antibodies and tetramethylbenzidine (TMB) substrate.

FIGS. 39-49 were produced utilizing the previously mentioned immunohistochemistry techniques. Anti-TK1 monoclonal antibodies were used to selectively stain cancerous tissues. Exponentially growing cancer cells, or normal cells were incubated with Oncoprev™ at room temperature, and stained using HRP-conjugated secondary antibodies. Cancer cells were incubated with buffer instead of Oncoprev™ as negative control (C). (All magnifications: 400×)

FDA Normal 33 Tissue Panel—FIG. 38

This research was contracted to Cybrdi of Washington, D.C. to obtain an independent evaluation of the antibodies' potential efficacy and toxicity. The FDA requires a panel of normal tissues before Phase I clinical trials. The data from the IFC, IFA, and FACS all demonstrate that the antibody will not be toxic to normal tissues in the body, even those that are rapidly dividing.

Cancer Panel

A panel of 18 different cancer tissues types was tested. With respect to, FIG. 43, samples were taken from patients at varying cancer stages, and the IFC results demonstrate a 26-fold increase in cell staining cancer cells versus normal controls. This confirms the FACS, IFA, internalization studies, shedding studies and comparison of TK1 to gp240.

In short, the tests have shown that no normal cells have surface TK1 and that cancerous cells all do, typically at least 1 million copies per cell. This discrepancy allows clinicians to exploit TK1 as a unique target for the treatment of all cancer types. It augurs well for the future of efforts in developing a humanized antibody that will not only extend the life of cancer patients, but add to survival rates as well Example 7

Flow Cytometer

Additional assays demonstrate that selected monoclonal antibodies bind specifically to cells producing TK1. Flow Cytometer plots were utilized to further characterize the ability of anti-TK1 antibodies to specifically target cancer cells.

Flow Cytometer plots were produced utilizing methods known in the art. Utilizing a test tube method, each sample was placed in two labeled 12×75 mm test tubes, one for the monoclonal antibody and the other for the appropriate control. Subsequently, 1×106 cells from the mononuclear cell preparation were placed in each test tube and centrifuged at 2-8° C. at 400-450×g for 4 min. The technician aspirated and discarded the supernatant.

Then, 200 μL of monoclonal antibody working solution or 200 μL of control working solution, respectively, was placed into the appropriately labeled test tubes. The reactions were vortexed gently. The reactions were incubated at 2-8° C. for 30-35 min.

Following incubation each reaction mixture was washed with 1 mL of 2-8° C. wash medium and centrifuged at 2-8° C. at 400-450×g for 4 min. Each reaction was aspirated carefully and the supernatant was discarded.

A vortex was used subsequently to disrupt cell pellets. The wash steps that followed incubation were repeated. After the second wash, the samples were aspirated carefully and the supernatant was discarded. Then 200 mL of GAM-FITC working solution or Avidin d-FITC working solution (for Biotin-labeled) was added to each cell pellet. The cell pellets were gently disrupted using a vortex.

The cells were incubated at 2-8° C. for 30-35 min. At the end of 30 min., the cells were washed three times with 1 mL of 2-8° C. resuspension medium. Each time the sample was centrifuged at 2-8° C. at 400-450×g for 4 min. The sample was then aspirated carefully and the supernatant was discarded. The cell pellets were then gently disrupted using a vortex.

The steps following the second incubation were repeated twice. After the third wash, the cells were resuspended by adding 1 mL of 2-8° C. resuspension medium to each test tube. The samples were transferred into appropriate containers for flow cytometry or fluorescence microscopy analysis. To ensure maximum viability, the stained cells were analyzed promptly.

Figure 31:
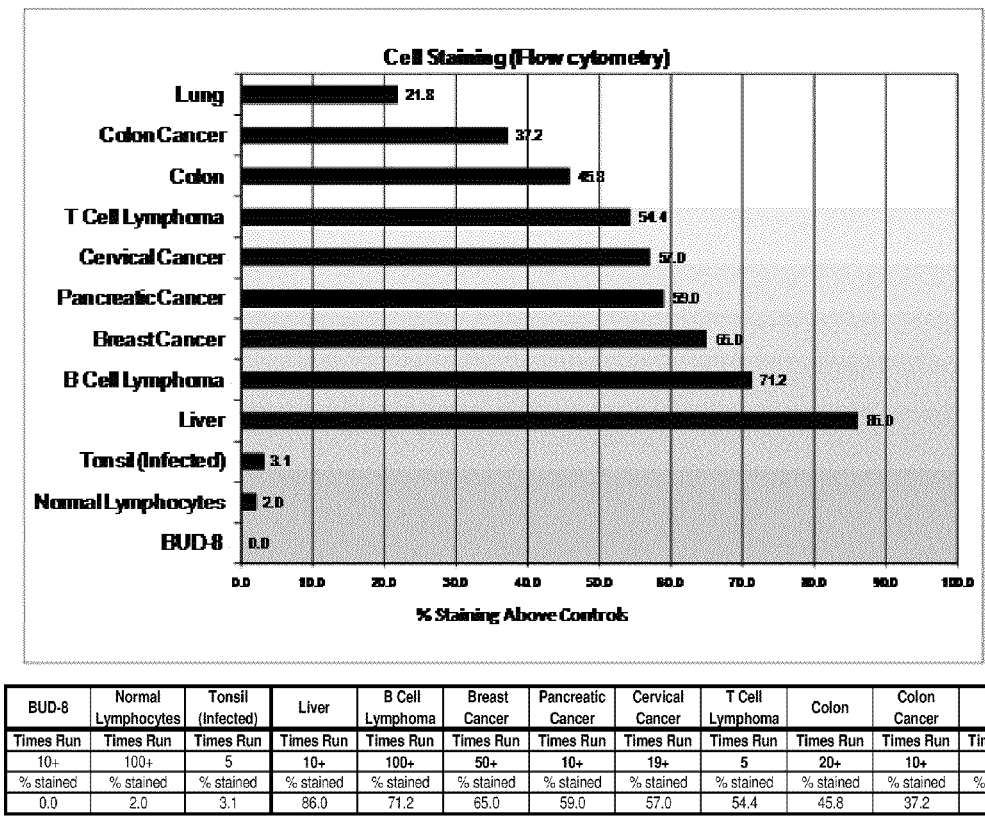
FIG. 31 is a bar graph and legend thereof, with samples, in the same order as the graph, comparing the amount of surface TK1 on various types of cells as indicated.

For the test of FIG. 31, blood was drawn from control patients without cancer to establish a baseline level against which to compare normal cells and known cancerous cell lines. Technicians ran the lymphocyte controls through the Flow Cytometer without the subject antibodies of interest and 10.1% or 4,510 of 44477 total cells were counted by the Flow Cytometer. This set the baseline level to compare unstained normal lymphocyte cells to lymphocyte cells stained with the antibody in accordance with the invention. The results show that only 12.1% of the lymphocyte controls or 2494 of 20628 were counted by the Flow Cytometer when normal lymphocyte cells were incubated with the subject Oncoprev™ monoclonal antibody. This result does not differ significantly from the control number of 10.1% and demonstrates that TK1 is not detected by our Oncoprev™ monoclonal antibody on the surface of the normal lymphocytes.

In FIG. 31, additional Flow Cytometer plots were produced for various cancer types. The cancer control cells were run through the Flow Cytometer without the subject antibodies and only 6.64% or 1,448 of 20302 total cells were counted by the Flow Cytometer. This set the baseline level to compare unstained cancer cells to cancer cells stained with the antibody.

These experiments shown in FIG. 31 were repeated with the following cancer cell types. The result demonstrates the universal nature of TK1 surface expression in cancers of all types including: breast cancer, cervical cancer, colon cancer, liver cancer, lung cancer, melanoma, pancreatic cancer and T-cell lymphoma.

Example 8

ELISA Measuring Surface TK1

Figure 32:
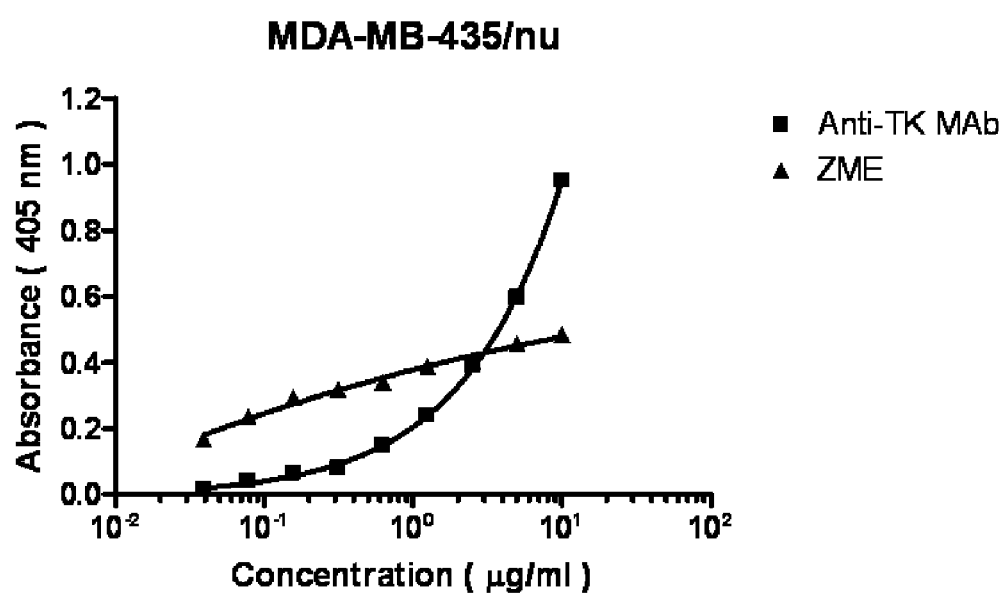
FIG. 32 is an Elisa graph comparing the amount of surface TK1 (shown by anti-TK1 MAb bound thereto) to the amount of protein gp240 (shown by the ZME-018 antibody bound thereto)

FIG. 32 shows breast cancer cells (MDA-MB-435/nu) were grown in 96 well micro-titer plates and stained with Anti-TK1 antibody, and with ZME-018, which binds gp240, acting as a positive control. The data demonstrate that surface TK1 is present in quantities that exceed gp240 at antibody concentrations of 2 g/ml (gp240 has been shown to have between 500,000 and 1,000,000 copies per cell).

Example 9

Internalization Studies

Figure 33:
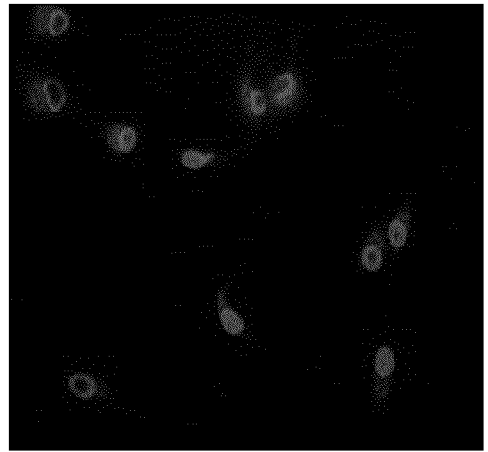
FIG. 33 is a photograph of a microscope slide of untreated cells (no antibody added) binding the secondary reagent non-specifically.
Figure 34:
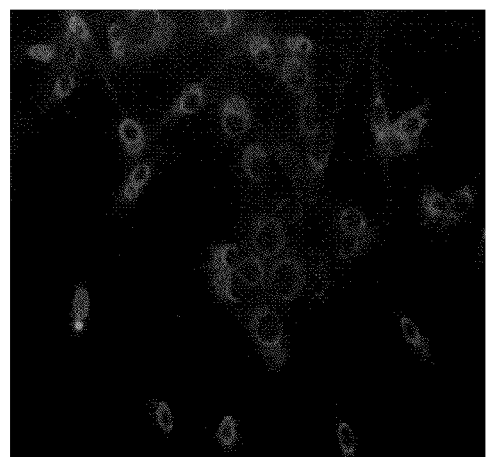
FIG. 34 is a photograph of a microscope slide showing antibody ZME-018 specifically binding gp240, which is then internalized in the cell as shown.
Figure 35:
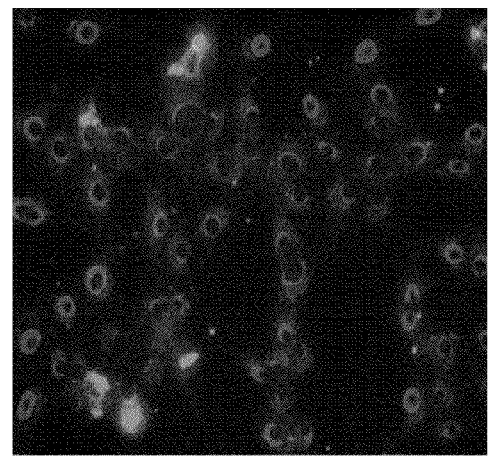
FIG. 35 is a photograph of a microscope slide showing an Anti-TK1 antibody specifically binding to the surface TK1, which is then internalized into the cell as shown.
Figure 39:
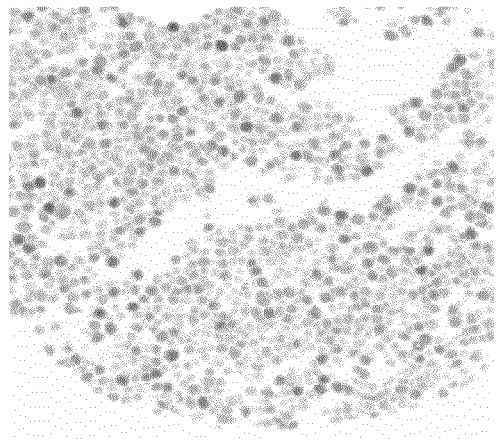
FIG. 39 is a photograph of a microscope slide showing salivary gland normal tissue failing to stain for presence of TK1, at 40×.
Figure 40:
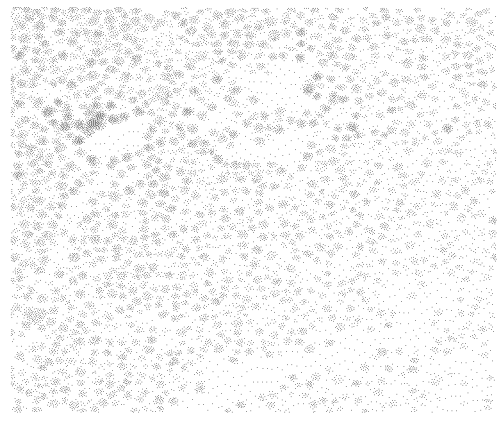
FIG. 40 is a photograph of a microscope slide showing the normal tissue bound with control antibody (positive control, mouse is type IgG) at 40×.
Figure 41:
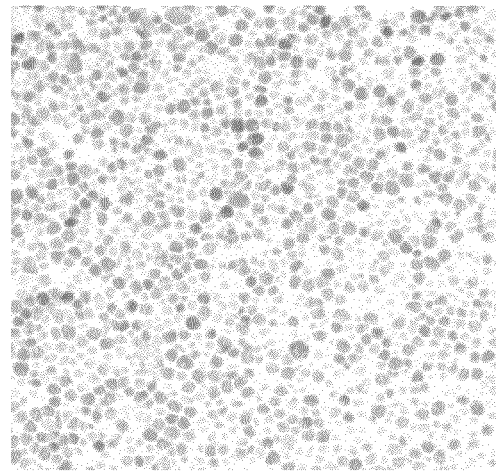
FIG. 41 is a photograph of a microscope slide showing intestinal tissue failing to bind to TK1 at 40×.
Figure 42:
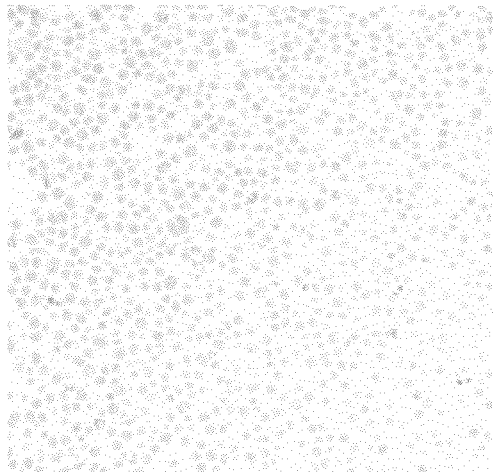
FIG. 42 is a photograph of a microscope slide showing intestinal tissue bound with positive control antibodies of FIG. 40, mIgG at 40×.
Figure 44:
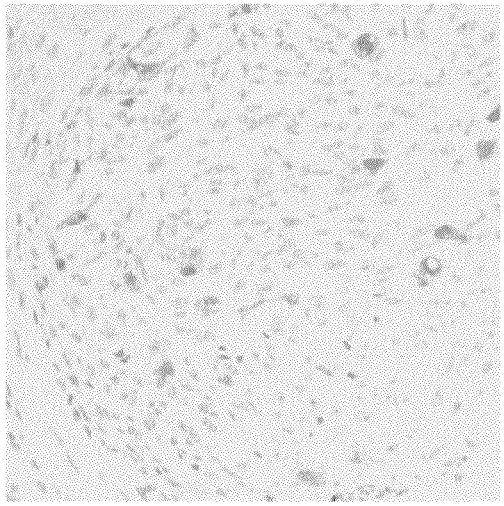
FIG. 44 is a photograph of a microscope slide of a sample of melanoma (cancerous skin tissue) with, TK1 bound to its cells, shown at 40×.
Figure 45:
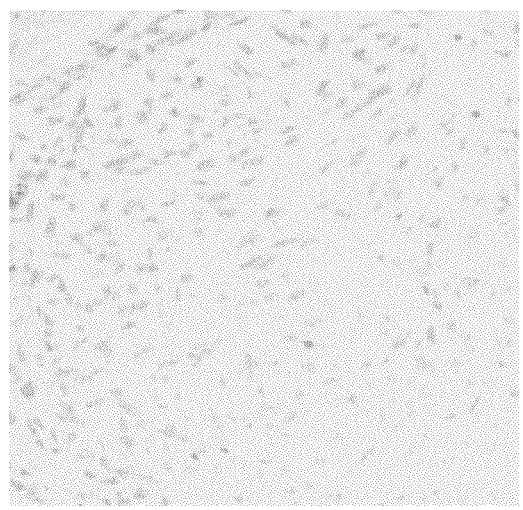
FIG. 45 is a photograph of a microscope slide of a sample of melanoma having a positive control antibody bound to its cells, shown at 40×.
Figure 46:
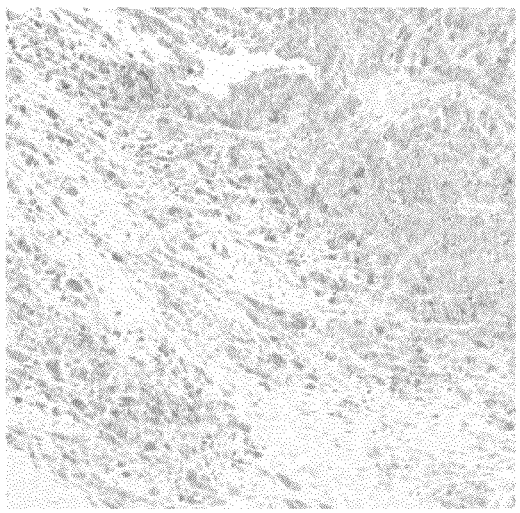
FIG. 46 is a photograph of a microscope slide of a sample of melanoma having TK1 bound to its cells shown at 20×.
Figure 47:
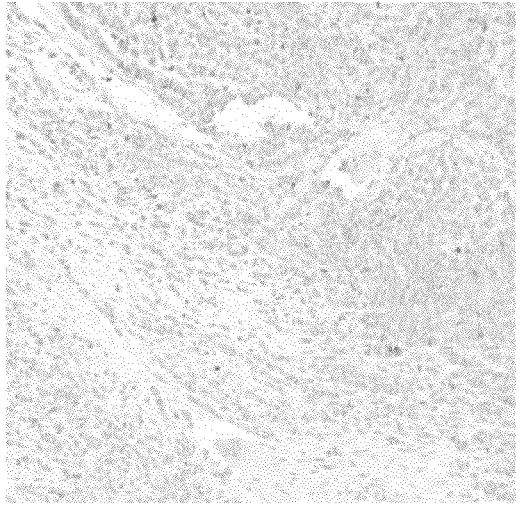
FIG. 47 is a photograph of a microscope slide of a sample of melanoma having a positive control antibody bound to its cells, shown at 20×.
Figure 48:
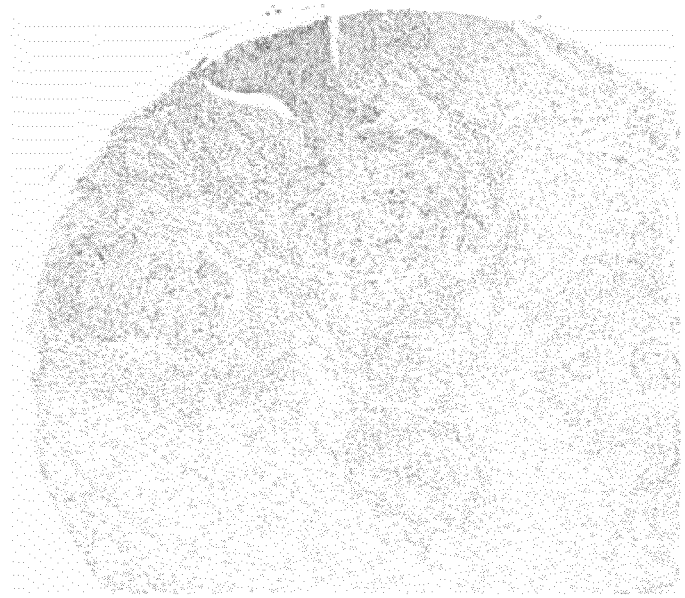
FIG. 48 is a photograph of a microscope slide of a sample of cervical cancer tissue having TK1 bound to its cells shown at 10×.
Figure 49:
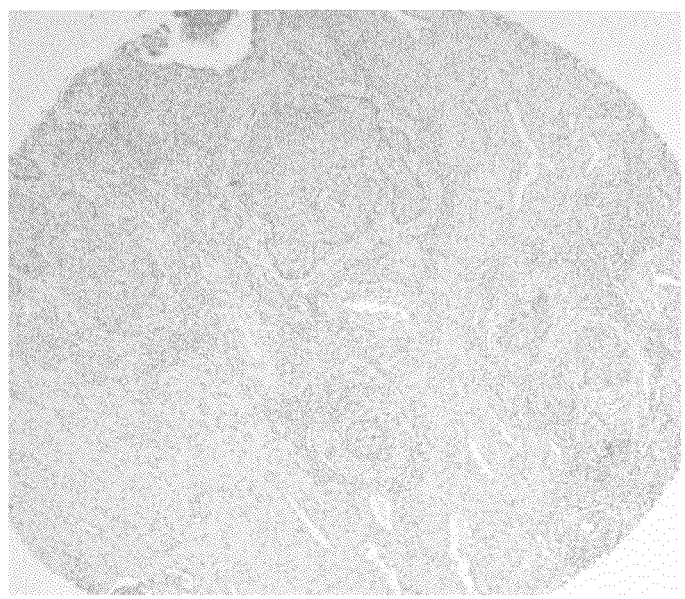
FIG. 49 is a photograph of a microscope slide of a sample of cervical cancer tissue having a positive control antibody bound to its cells, shown at 10×.

Referring to FIG. 33 breast cancer cells (MDA-MB-435/nu) were grown in 96 well micro-titer plates and stained with Anti-TK1 antibody, and with ZME-018, which binds gp240, acting as a positive control. FIGS. 34 and 35 demonstrate that Anti-TK1 antibodies are internalized into breast cancer cells, which makes them a candidate for cell killing by coupling the subject antibody to a toxin.

Example 10

Murine Tumor Xenograft—Colon Cancer

Referring to FIGS. 36 and 37, tests show that anti-TK1 antibodies are efficacious in more than one type of xenograft model. The following xenograft to Colon cancer in FIG. 36, which is much different from breast cancer of FIG. 37, provides proof. Furthermore, the greater the expression of surface TK1 the more efficacious the subject anti-TK1 antibody was. Also note in the literature that humanization increases ADCC and CDC on average ten-fold and that the research is current. It is inappropriate to rely on decades old research in opposite that it predates granting of the first patent for a material for treatment of humans over-expressing a surface antigen, namely the product Rituxan™, produced and sold by Genentech.

Murine Tumor Xenograft—Breast Cancer

Example 11

Anti-TK1 Utilized in Complement Mediated Lysis

In one therapeutic application for anti-TK1 monoclonal antibodies, the anti-TK1 antibody is useful for targeted tumor therapy. The bound anti-TK1 antibodies may be utilized to initiate complement mediated lysis destroying the cancerous cells.

This embodiment is particularly effective because the anti-TK1 antibody binds specifically to tumor cells expressing large amounts of TK1. Because the anti-TK1 antibody binds specifically to tumor cells expressing large amount of TK1, it is targeted specifically to tumor cells. The killing of these tumor cells by complement mediated lysis is preferentially enhanced relative to the killing of normal cells.

Additionally, TK1, unlike most other cancer markers, which are specific to only one type of cancer, acts as a useful cancer marker in many types of cancer. Complement mediated lysis is a process well understood. The selection of an appropriate complement pathway may be used with an embodiment of a treatment in accordance with the invention.

An example of a protocol for complement mediated lysis targeted by anti-TK1 is comprised of the following steps. First, 2 mls of Raji cells are removed from a culture kept between $5 \times 10^5$ and $1 \times 10^6$ cells per ml from culture. The cells are centrifuged at 1600 rpm for 10 minutes. The supernatant is discarded. Subsequently, the cells are washed three times with PBS. The hybridoma supernatant is diluted with PBS by a dilution factor of 1:2.

The cells are then incubated in diluted supernatant for one hour on ice. After one hour, the cells are washed three times and resuspend in one ml of PBS. Then 3 mls of serum is added to cells, and 3 mls of PBS to control cells. The cells are placed in a 370 water bath for one hour. The cells are subsequently removed from the waterbath and placed on a microscope slide for observation.

Figure 23:
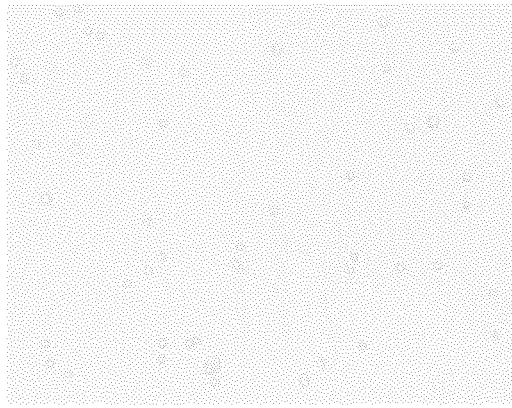
FIG. 23 is a photograph of a microscope slide of Raji cells (B-cell lymphoma) with CB101 IgM antibody without serum at a concentration of 1.1 million cells/ml.
Figure 24:
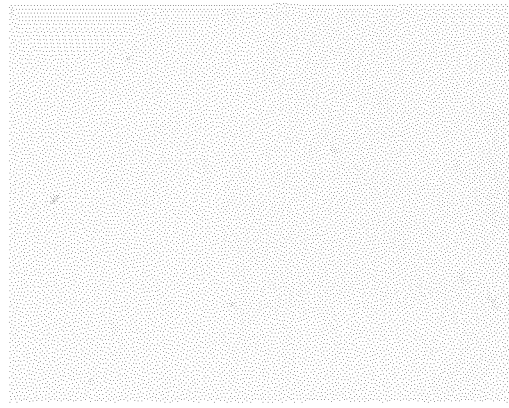
FIG. 24 is a photograph of a microscope slide of Raji cells with CB101 IgM and serum demonstrating greater than 96% lysis.

FIGS. 23 and 24 show photos produced utilizing the aforementioned protocol. FIGS. 23 and 24 demonstrate that cancerous B cells (Raji) are lysed by complement when the TK1 antibody binds to the surface. FIG. 23 is a picture of the control Raji cells, and FIG. 24 is a picture of the cancerous B cells (Raji) destroyed by complement mediated lysis.

Example 12

Utilizing Anti-TK1 to Target and Destroy Cancerous Cells

A variety of therapeutic applications are possible based on the knowledge that TK1 is found on the surface of cancerous cells. For example, an anti-cancer drug may selectively target and kill cells expressing TK1 on the cell surface. This tactic is exemplified by cancer therapies that use Adenoviruses to infect cells with a plasmid that encodes a viral TK1 gene. This gene may then be targeted to be killed by interrupting DNA synthesis. This embodiment is further exemplified by the therapeutic application of anti-TK1 antibodies, which comprises anti-TK1 antibodies coupled with anti-tumor agents. An anti-tumor agent is coupled to the anti-TK1 antibody, which enhances the cytotoxic effects of the anti-TK1 antibody, and thus the killing of tumor cells relative to the killing of normal cells.

Example 13

Anti-TK1 Binding of TK1 to Reduce Proliferation of Cancer

Additionally, this invention contemplates using anti-TK1 antibodies, and particularly the anti-TK1 antibody, which may be useful for targeted therapy. For example, the anti-TK1 antibody is used to inhibit the elevated levels of TK1 and to restore a normal level of TK1, which helps reduce cellular replication. The anti-TK1 antibody may be used to inhibit the elevated level and to restore a normal level of TK1 enzyme activity in the tumor cells, which may decrease cellular proliferation and halt spread of the disease.

An example of this embodiment comprises the use of anti-TK1 monoclonal antibodies used as a therapeutic agent, to bind TK1 in cancer patients and reduce proliferation. Because TK1 is a salvage pathway enzyme, treatment with anti-TK1 monoclonal antibody has minor effects on normal tissue and allows all cells that proliferate by the normal pathway to divide normally and leave non-proliferating cells unharmed.

Example 14

Therapeutic Site Directed Surgery

Another therapeutic application contemplated by this invention is the use of anti-TK1 antibody, which may also be useful for site directed surgery. Dye and isotope directed surgeries techniques are known. Because anti-TK1 antibodies adhere to the surface of cancerous cells, the FiguresS demonstrate using anti-TK1 antibodies to clearly mark cancerous tissues. Thus, the cancerous tissues can be identified, visually or otherwise, by a surgeon who may then excise or destroy cancerous tissue utilizing conventional, minimally invasive, surgical techniques.

Example 15

Kits Which Utilize Monoclonal Antibodies for Therapeutic Purposes

Further, the invention contemplates using methods and kits for performing methods. A kit for performing the above methods may comprise one or more monoclonal antibodies, for example, anti-TK1 to 2 different epitopes on TK1. In one embodiment, the monoclonal antibody may be conjugated with or packaged in conjunction with other agents, for example anti-tumor agents or commercially available complement. These may be administered to have therapeutic effects on the intended patients.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

The invention claimed is:

1. A method for treating cancer characterized by increased expression of TK1 on the surface of cancer cells in a mammal, the method comprising administering to the mammal a therapeutically effective amount of a pharmaceutical composition comprising at least one of an anti-TK1 antibody and a TK1-binding fragment of the anti-TK1 antibody which is effective to inhibit cellular replication of cancer cells and/or kill cancer cells, wherein the anti-TK1 antibody is a monoclonal antibody.

2. The method of claim 1, wherein the anti-TK1 antibody is selected from a humanized and a fully human monoclonal antibody.

3. The method of claim 1, further comprising treating the mammal with an amount of radiation effective to up-regulate TK1 expression, prior to administering the pharmaceutical composition.

4. The method of claim 1, wherein the pharmaceutical composition further comprises a pharmaceutically acceptable liquid carrier adapted for parenteral administration.

5. The method of claim 4, wherein the liquid carrier comprises isotonic saline.

6. The method of claim 1 wherein: the method further comprises introducing into the bloodstream a quantity of an anti-TK1 antibody coupled with an anti-tumor agent, sufficiently cytotoxic to preferentially kill tumor cells compared to normal cells.

7. The method of claim 1, further comprising inhibiting the elevated level of TK1 enzyme activity, decreasing cellular proliferation, and slowing the spread of the cancer by introducing a quantity of an anti-TK1 antibody into the bloodstream.

* * * * *

UNITED STATES PATENT AND TRADEMARK OFFICE
CERTIFICATE OF CORRECTION

| | | |
|---|---|---|
| PATENT NO. | : 8,551,486 B2 | Page 1 of 1 |
| APPLICATION NO. | : 12/328379 | |
| DATED | : October 8, 2013 | |
| INVENTOR(S) | : Lallatin | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 467 days.

Signed and Sealed this
Twentieth Day of May, 2014

Michelle K. Lee
*Deputy Director of the United States Patent and Trademark Office*